(12) United States Patent
Hunt et al.

(10) Patent No.: US 12,011,942 B2
(45) Date of Patent: Jun. 18, 2024

(54) RULES FOR SENSOR INTEGRATED SUBSTRATES

(71) Applicant: Smith & Nephew PLC, Watford (GB)

(72) Inventors: Allan Kenneth Frazer Grugeon Hunt, Beverley (GB); Lee Ian Partington, Hessle (GB); Marcus Damian Phillips, Wakefield (GB); Felix Clarence Quintanar, Hull (GB)

(73) Assignee: Smith & Nephew PLC, Watford (GB)

( * ) Notice: Subject to any disclaimer, the term of this patent is extended or adjusted under 35 U.S.C. 154(b) by 267 days.

(21) Appl. No.: 17/440,679

(22) PCT Filed: Mar. 16, 2020

(86) PCT No.: PCT/EP2020/057145
§ 371 (c)(1),
(2) Date: Sep. 17, 2021

(87) PCT Pub. No.: WO2020/187851
PCT Pub. Date: Sep. 24, 2020

(65) Prior Publication Data
US 2022/0176722 A1    Jun. 9, 2022

(30) Foreign Application Priority Data

Mar. 18, 2019   (GB) ..................................... 1903661
Dec. 17, 2019   (GB) ..................................... 1918640

(51) Int. Cl.
*H05K 1/00*       (2006.01)
*B41M 1/12*       (2006.01)
(Continued)

(52) U.S. Cl.
CPC .............. *B41M 3/006* (2013.01); *B41M 1/12* (2013.01); *H05K 1/028* (2013.01); *H05K 1/092* (2013.01);
(Continued)

(58) Field of Classification Search
CPC .................................. H05K 3/00; H05K 1/00
See application file for complete search history.

(56) References Cited

U.S. PATENT DOCUMENTS

| 3,896,802 A | 7/1975 | Williams |
| 4,334,530 A | 6/1982 | Hassell |

(Continued)

FOREIGN PATENT DOCUMENTS

| CN | 105232229 A | 1/2016 |
| CN | 105395184 A | 3/2016 |

(Continued)

OTHER PUBLICATIONS

Aubakir B., et al., "Vital Sign Monitoring Utilizing Eulerian Video Magnification and Thermography," 38th Annual International Conference of the IEEE Engineering in Medicine and Biology Society, Aug. 16, 2016, pp. 3527-3530 (4 pages).

(Continued)

*Primary Examiner* — Kelly M Gambetta
*Assistant Examiner* — Mohammad Mayy
(74) *Attorney, Agent, or Firm* — Knobbe, Martens, Olson & Bear, LLP

(57) ABSTRACT

Methods of manufacturing a wound monitoring and/or therapy apparatus and/or wound dressing include positioning electronic components and connections in regions of a substrate that are not configured to be perforated. The methods can also include following a set of rules for positioning the components as well as positioning and shaping the connections based on the constraints stemming from, among other things, the positioning of the perforations on the substrate and with the goal of maintaining acceptable levels of signal integrity. The methods further include manu- (Continued)

facturing a multi-layered substrate. Wound monitoring and/or therapy apparatus manufactured using such methods are also disclosed.

20 Claims, 15 Drawing Sheets

(51) Int. Cl.
| | |
|---|---|
| *B41M 3/00* | (2006.01) |
| *H05K 1/02* | (2006.01) |
| *H05K 1/09* | (2006.01) |
| *H05K 3/12* | (2006.01) |
| *A61F 13/00* | (2006.01) |

(52) U.S. Cl.
CPC ...... *H05K 3/1216* (2013.01); *A61F 13/00051* (2013.01); *H05K 2201/10151* (2013.01)

(56) References Cited

U.S. PATENT DOCUMENTS

| | | | |
|---|---|---|---|
| 5,090,410 A | 2/1992 | Saper et al. |
| 5,253,654 A | 10/1993 | Thomas et al. |
| 5,635,201 A | 6/1997 | Fabo |
| 5,642,096 A | 6/1997 | Leyerer et al. |
| 5,678,448 A | 10/1997 | Fullen et al. |
| 5,690,610 A | 11/1997 | Ito et al. |
| 5,836,990 A | 11/1998 | Li |
| 6,095,992 A | 8/2000 | Augustine |
| 6,178,342 B1 | 1/2001 | Borgos et al. |
| 6,381,482 B1 | 4/2002 | Jayaraman et al. |
| 6,517,484 B1 | 2/2003 | Wilk et al. |
| 6,551,252 B2 | 4/2003 | Sackner et al. |
| 6,731,987 B1 | 5/2004 | McAdams et al. |
| 7,077,832 B2 | 7/2006 | Fleischmann |
| 7,088,591 B2 | 8/2006 | Kishimoto et al. |
| 7,201,063 B2 | 4/2007 | Taylor |
| 7,206,623 B2 | 4/2007 | Blank et al. |
| 7,289,205 B2 | 10/2007 | Yaroslavsky et al. |
| 7,316,652 B2 | 1/2008 | Dalgaard et al. |
| 7,429,255 B2 | 9/2008 | Thompson |
| 7,520,875 B2 | 4/2009 | Bernabei |
| 7,521,292 B2 | 4/2009 | Rogers et al. |
| 7,569,742 B2 | 8/2009 | Haggstrom et al. |
| 7,625,117 B2 | 12/2009 | Haslett et al. |
| 7,687,678 B2 | 3/2010 | Jacobs |
| 7,846,141 B2 | 12/2010 | Weston |
| 7,877,866 B1 | 2/2011 | Greenberg et al. |
| 7,884,258 B2 | 2/2011 | Boehringer et al. |
| 7,904,133 B2 | 3/2011 | Gehman et al. |
| 7,922,676 B2 | 4/2011 | Daskal et al. |
| 7,942,869 B2 | 5/2011 | Houbolt et al. |
| 7,945,302 B2 | 5/2011 | McAdams |
| 8,019,401 B1 | 9/2011 | Smith et al. |
| 8,032,210 B2 | 10/2011 | Finneran et al. |
| 8,060,174 B2 | 11/2011 | Simpson et al. |
| 8,079,247 B2 | 12/2011 | Russell et al. |
| 8,111,165 B2 | 2/2012 | Ortega et al. |
| 8,116,841 B2 | 2/2012 | Bly et al. |
| 8,182,425 B2 | 5/2012 | Stamatas et al. |
| 8,238,996 B2 | 8/2012 | Burnes et al. |
| 8,241,231 B2 | 8/2012 | Bausewein et al. |
| 8,332,053 B1 | 12/2012 | Patterson et al. |
| 8,333,874 B2 | 12/2012 | Currie |
| 8,366,692 B2 | 2/2013 | Weston et al. |
| 8,480,641 B2 | 7/2013 | Jacobs |
| 8,525,340 B2 | 9/2013 | Eckhardt et al. |
| 8,579,872 B2 | 11/2013 | Coulthard et al. |
| 8,644,911 B1 | 2/2014 | Panasyuk et al. |
| 8,663,106 B2 | 3/2014 | Stivoric et al. |
| 8,682,442 B2 | 3/2014 | McAdams |
| 8,783,948 B2 | 7/2014 | Panda et al. |
| 8,788,009 B2 | 7/2014 | Greene et al. |
| 8,800,386 B2 | 8/2014 | Taylor |
| 8,818,478 B2 | 8/2014 | Scheffler et al. |
| 8,848,187 B2 | 9/2014 | Uematsu et al. |
| 8,894,590 B2 | 11/2014 | Lamoise et al. |
| 8,925,392 B2 | 1/2015 | Esposito et al. |
| 8,934,957 B2 | 1/2015 | Dias et al. |
| 8,934,965 B2 | 1/2015 | Rogers et al. |
| 8,943,897 B2 | 2/2015 | Beauvais et al. |
| 8,948,839 B1 | 2/2015 | Longinotti-Buitoni et al. |
| 8,997,588 B2 | 4/2015 | Taylor |
| 9,000,251 B2 | 4/2015 | Murphy et al. |
| 9,042,075 B2 | 5/2015 | Borini et al. |
| 9,192,531 B2 | 11/2015 | Wu |
| 9,220,455 B2 | 12/2015 | Sarrafzadeh et al. |
| 9,226,402 B2 | 12/2015 | Hsu |
| 9,282,897 B2 | 3/2016 | Ross, Jr. et al. |
| 9,314,175 B2 | 4/2016 | Jacofsky et al. |
| 9,320,473 B2 | 4/2016 | Shuler |
| 9,372,123 B2 | 6/2016 | Li et al. |
| 9,378,450 B1 | 6/2016 | Mei et al. |
| 9,380,698 B1 | 6/2016 | Li et al. |
| 9,386,947 B2 | 7/2016 | Johnson |
| 9,393,354 B2 | 7/2016 | Freedman et al. |
| 9,402,988 B2 | 8/2016 | Buchanan et al. |
| 9,408,573 B2 | 8/2016 | Welch et al. |
| 9,427,179 B2 | 8/2016 | Mestrovic et al. |
| 9,439,599 B2 | 9/2016 | Thompson et al. |
| 9,483,726 B2 | 11/2016 | Mei et al. |
| 9,494,474 B2 | 11/2016 | Servati et al. |
| 9,511,215 B2 | 12/2016 | Skiba |
| 9,516,758 B2 | 12/2016 | Arora et al. |
| 9,526,439 B2 | 12/2016 | Connelly et al. |
| 9,554,484 B2 | 1/2017 | Rogers et al. |
| 9,572,507 B2 | 2/2017 | Moore et al. |
| 9,582,072 B2 | 2/2017 | Connor |
| 9,585,620 B2 | 3/2017 | Paquet et al. |
| 9,587,991 B2 | 3/2017 | Padiy |
| 9,592,007 B2 | 3/2017 | Nuovo et al. |
| 9,603,560 B2 | 3/2017 | Monty et al. |
| 9,610,388 B2 | 4/2017 | Aceto et al. |
| 9,613,911 B2 | 4/2017 | Rogers et al. |
| 9,629,584 B2 | 4/2017 | Macia Barber et al. |
| 9,675,238 B2 | 6/2017 | Iida et al. |
| 9,687,195 B2 | 6/2017 | Sims et al. |
| 9,717,565 B2 | 8/2017 | Blair |
| 9,829,471 B2 | 11/2017 | Hammond et al. |
| 9,907,103 B2 | 2/2018 | Chen et al. |
| 10,004,643 B2 | 6/2018 | Luckemeyer et al. |
| 10,046,096 B2 | 8/2018 | Askem et al. |
| 10,080,524 B1 | 9/2018 | Xi |
| 10,086,117 B2 | 10/2018 | Locke et al. |
| 10,117,705 B2 | 11/2018 | Chernov et al. |
| 10,152,789 B2 | 12/2018 | Carnes et al. |
| 10,166,387 B2 | 1/2019 | Bergelin et al. |
| 10,182,740 B2 | 1/2019 | Tonar et al. |
| 10,206,604 B2 | 2/2019 | Bergelin et al. |
| 10,207,031 B2 | 2/2019 | Toth |
| 10,209,213 B2 | 2/2019 | Kang et al. |
| 10,285,620 B2 | 5/2019 | Jung et al. |
| 10,321,862 B2 | 6/2019 | Dalene et al. |
| 10,463,773 B2 | 11/2019 | Haggstrom et al. |
| 10,687,984 B2 | 6/2020 | Rovaniemi |
| 10,702,153 B2 | 7/2020 | Shamim et al. |
| 10,716,490 B2 | 7/2020 | Connolly |
| 10,857,038 B2 | 12/2020 | Zamierowski et al. |
| 11,026,847 B2 | 6/2021 | Piotrowski et al. |
| 11,647,922 B2 | 5/2023 | Scherer |
| 11,850,121 B2 | 12/2023 | Rapp |
| 2002/0016536 A1 | 2/2002 | Benni |
| 2002/0135752 A1 | 9/2002 | Sokolov et al. |
| 2003/0033032 A1 | 2/2003 | Lind et al. |
| 2003/0208148 A1 | 11/2003 | Sullivan |
| 2003/0210810 A1 | 11/2003 | Gee, Jr. et al. |
| 2003/0216630 A1 | 11/2003 | Jersey-Willuhn et al. |
| 2004/0230132 A1 | 11/2004 | Shehada |
| 2005/0088832 A1 | 4/2005 | Su et al. |
| 2005/0240107 A1 | 10/2005 | Alfano et al. |
| 2005/0280531 A1 | 12/2005 | Fadem et al. |
| 2006/0052678 A1 | 3/2006 | Drinan et al. |
| 2006/0058690 A1 | 3/2006 | Bartnik et al. |

(56) References Cited

U.S. PATENT DOCUMENTS

| | | |
|---|---|---|
| 2006/0181791 A1 | 8/2006 | Van Beek et al. |
| 2006/0234383 A1 | 10/2006 | Gough |
| 2006/0241495 A1 | 10/2006 | Kurtz |
| 2007/0055209 A1 | 3/2007 | Patel et al. |
| 2007/0173892 A1 | 7/2007 | Fleischer et al. |
| 2007/0191754 A1 | 8/2007 | Aali |
| 2007/0260421 A1 | 11/2007 | Berner, Jr. et al. |
| 2007/0293748 A1 | 12/2007 | Engvall et al. |
| 2008/0054408 A1 | 3/2008 | Tippey et al. |
| 2008/0062112 A1* | 3/2008 | Umezaki ............ H01L 27/156 345/100 |
| 2008/0081973 A1 | 4/2008 | Hoarau |
| 2008/0167535 A1 | 7/2008 | Stivoric et al. |
| 2008/0258717 A1 | 10/2008 | Igney et al. |
| 2008/0287747 A1 | 11/2008 | Mestrovic et al. |
| 2008/0319282 A1 | 12/2008 | Tran |
| 2008/0319283 A1 | 12/2008 | Cotton et al. |
| 2009/0149800 A1* | 6/2009 | Durand ............ A61N 1/37247 717/109 |
| 2009/0163819 A1* | 6/2009 | De Kok ............ A61B 5/14551 600/476 |
| 2009/0177051 A1 | 7/2009 | Arons et al. |
| 2009/0177110 A1 | 7/2009 | Lyden et al. |
| 2009/0209830 A1 | 8/2009 | Nagle et al. |
| 2009/0234206 A1 | 9/2009 | Gaspard et al. |
| 2009/0245601 A1 | 10/2009 | Cohen et al. |
| 2010/0022990 A1 | 1/2010 | Karpowicz et al. |
| 2010/0025831 A1 | 2/2010 | Yamazaki et al. |
| 2010/0166252 A1 | 7/2010 | Ahmed et al. |
| 2010/0168727 A1 | 7/2010 | Hancock et al. |
| 2010/0305473 A1 | 12/2010 | Yuzhakov |
| 2011/0004088 A1 | 1/2011 | Grossman |
| 2011/0015591 A1 | 1/2011 | Hanson et al. |
| 2011/0054283 A1 | 3/2011 | Shuler |
| 2011/0130697 A1 | 6/2011 | Nagle et al. |
| 2011/0140703 A1 | 6/2011 | Chiao et al. |
| 2011/0190639 A1 | 8/2011 | Peltie et al. |
| 2011/0218757 A1 | 9/2011 | Callsen et al. |
| 2011/0242532 A1 | 10/2011 | McKenna |
| 2011/0245682 A1 | 10/2011 | Robinson et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0119912 A1* | 5/2012 | Ortega ............ G08B 21/0461 340/573.5 |
| 2012/0165717 A1 | 6/2012 | Al Khaburi |
| 2012/0190989 A1 | 7/2012 | Kaiser et al. |
| 2012/0265120 A1 | 10/2012 | Beisang, III et al. |
| 2012/0271265 A1 | 10/2012 | Langdon |
| 2012/0277559 A1 | 11/2012 | Kohl-Bareis et al. |
| 2012/0316538 A1 | 12/2012 | Heiser et al. |
| 2012/0330252 A1 | 12/2012 | Stokes et al. |
| 2013/0041235 A1 | 2/2013 | Rogers et al. |
| 2013/0064772 A1 | 3/2013 | Swiss et al. |
| 2013/0121544 A1 | 5/2013 | Sarrafzadeh et al. |
| 2013/0123722 A1 | 5/2013 | Pratt et al. |
| 2013/0151223 A1 | 6/2013 | Zamierowski et al. |
| 2013/0200268 A1 | 8/2013 | Rafferty et al. |
| 2013/0261409 A1 | 10/2013 | Pathak et al. |
| 2013/0271278 A1 | 10/2013 | Duesterhoft et al. |
| 2013/0274563 A1 | 10/2013 | Duesterhoft et al. |
| 2013/0274629 A1 | 10/2013 | Duesterhoft et al. |
| 2013/0317367 A1 | 11/2013 | Shuler |
| 2014/0012108 A1 | 1/2014 | McPeak |
| 2014/0018637 A1 | 1/2014 | Bennett et al. |
| 2014/0024905 A1 | 1/2014 | Sarrafzadeh et al. |
| 2014/0031663 A1 | 1/2014 | Gallego et al. |
| 2014/0072190 A1 | 3/2014 | Wu et al. |
| 2014/0075658 A1 | 3/2014 | McGuin |
| 2014/0107495 A1 | 4/2014 | Marinelli et al. |
| 2014/0107498 A1 | 4/2014 | Bower et al. |
| 2014/0147611 A1 | 5/2014 | Ackerman, Jr. |
| 2014/0203797 A1 | 7/2014 | Stivoric et al. |
| 2014/0206947 A1 | 7/2014 | Isserow et al. |
| 2014/0232516 A1 | 8/2014 | Stivoric et al. |
| 2014/0235166 A1 | 8/2014 | Molettiere et al. |
| 2014/0243709 A1 | 8/2014 | Gibson et al. |
| 2014/0296749 A1 | 10/2014 | Reid, Jr. et al. |
| 2014/0298927 A1 | 10/2014 | Allin et al. |
| 2014/0298928 A1 | 10/2014 | Duesterhoft et al. |
| 2014/0303463 A1 | 10/2014 | Robinson et al. |
| 2014/0324120 A1 | 10/2014 | Bogie et al. |
| 2014/0340857 A1 | 11/2014 | Hsu et al. |
| 2014/0343478 A1 | 11/2014 | Brennan et al. |
| 2014/0350882 A1 | 11/2014 | Everett et al. |
| 2015/0018792 A1 | 1/2015 | Marsiquet et al. |
| 2015/0025343 A1 | 1/2015 | Gareau et al. |
| 2015/0138330 A1 | 5/2015 | Krishnamoorthi |
| 2015/0141767 A1 | 5/2015 | Rogers et al. |
| 2015/0148760 A1 | 5/2015 | Dodd et al. |
| 2015/0150479 A1 | 6/2015 | Yoshino et al. |
| 2015/0182166 A1 | 7/2015 | Evans et al. |
| 2015/0223716 A1 | 8/2015 | Korkala et al. |
| 2015/0257644 A1 | 9/2015 | Cao |
| 2015/0265191 A1 | 9/2015 | Harding et al. |
| 2015/0292968 A1 | 10/2015 | Vogt et al. |
| 2015/0313476 A1 | 11/2015 | Pisani et al. |
| 2015/0313533 A1 | 11/2015 | Rapp et al. |
| 2015/0327777 A1 | 11/2015 | Kostic et al. |
| 2015/0335254 A1 | 11/2015 | Fastert et al. |
| 2015/0335287 A1 | 11/2015 | Neuman et al. |
| 2015/0335288 A1 | 11/2015 | Toth et al. |
| 2015/0351970 A1 | 12/2015 | Dagger et al. |
| 2015/0359485 A1 | 12/2015 | Berg et al. |
| 2015/0374309 A1 | 12/2015 | Farkas et al. |
| 2016/0015962 A1 | 1/2016 | Shokoueinejad Maragheh et al. |
| 2016/0022223 A1 | 1/2016 | Grundfest et al. |
| 2016/0029900 A1 | 2/2016 | LaPlante et al. |
| 2016/0030132 A1 | 2/2016 | Cheung et al. |
| 2016/0038045 A1 | 2/2016 | Shapiro |
| 2016/0038083 A1 | 2/2016 | Ding et al. |
| 2016/0051147 A1 | 2/2016 | Cohen et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |
| 2016/0074234 A1 | 3/2016 | Abichandani et al. |
| 2016/0081601 A1 | 3/2016 | Ballam et al. |
| 2016/0100790 A1 | 4/2016 | Cantu et al. |
| 2016/0100987 A1 | 4/2016 | Hartwell et al. |
| 2016/0129469 A1 | 5/2016 | Kulinsky et al. |
| 2016/0143534 A1 | 5/2016 | Hyde et al. |
| 2016/0157779 A1 | 6/2016 | Baxi et al. |
| 2016/0213269 A1 | 7/2016 | Lam et al. |
| 2016/0228049 A1 | 8/2016 | Nackaerts et al. |
| 2016/0232807 A1 | 8/2016 | Ghaffari et al. |
| 2016/0242331 A1 | 8/2016 | Park et al. |
| 2016/0249810 A1 | 9/2016 | Darty et al. |
| 2016/0262672 A1 | 9/2016 | Hammond et al. |
| 2016/0262687 A1 | 9/2016 | Vaidyanathan et al. |
| 2016/0270700 A1 | 9/2016 | Baxi et al. |
| 2016/0287177 A1 | 10/2016 | Huppert et al. |
| 2016/0302729 A1 | 10/2016 | Starr et al. |
| 2016/0310023 A1 | 10/2016 | Chachisvilis et al. |
| 2016/0317057 A1 | 11/2016 | Li et al. |
| 2016/0331263 A1 | 11/2016 | Cailler et al. |
| 2016/0331322 A1 | 11/2016 | Son et al. |
| 2016/0338591 A1 | 11/2016 | Lachenbruch et al. |
| 2016/0354001 A1 | 12/2016 | Buckley et al. |
| 2016/0367189 A1 | 12/2016 | Aimone et al. |
| 2016/0367192 A1 | 12/2016 | Iyengar et al. |
| 2016/0367406 A1 | 12/2016 | Barnett |
| 2017/0000407 A1 | 1/2017 | Saxby et al. |
| 2017/0007853 A1 | 1/2017 | Alford et al. |
| 2017/0027498 A1 | 2/2017 | Larson et al. |
| 2017/0079740 A1 | 3/2017 | Hufnagel et al. |
| 2017/0086519 A1 | 3/2017 | Vigano' et al. |
| 2017/0086709 A1 | 3/2017 | Khine et al. |
| 2017/0095208 A1 | 4/2017 | Oberleitner et al. |
| 2017/0146474 A1 | 5/2017 | Bedell et al. |
| 2017/0156594 A1 | 6/2017 | Stivoric et al. |
| 2017/0156621 A1 | 6/2017 | Bettinger et al. |
| 2017/0156658 A1 | 6/2017 | Maharbiz et al. |
| 2017/0164865 A1 | 6/2017 | Rafferty et al. |

(56) References Cited

U.S. PATENT DOCUMENTS

| | | |
|---|---|---|
| 2017/0164876 A1 | 6/2017 | Hyde et al. |
| 2017/0172439 A1 | 6/2017 | Zhu et al. |
| 2017/0202711 A1 | 7/2017 | Cernasov et al. |
| 2017/0224271 A1 | 8/2017 | Lachenbruch et al. |
| 2017/0231015 A1 | 8/2017 | Jang et al. |
| 2017/0258972 A1 | 9/2017 | Weston |
| 2017/0319075 A1 | 11/2017 | Homan et al. |
| 2017/0326004 A1 | 11/2017 | Long et al. |
| 2017/0367644 A1 | 12/2017 | Sharman et al. |
| 2018/0003579 A1 | 1/2018 | Esposito et al. |
| 2018/0008177 A1 | 1/2018 | Shimuta et al. |
| 2018/0055697 A1 | 3/2018 | Mihali et al. |
| 2018/0056087 A1* | 3/2018 | Ribeiro ............ A61L 15/00 |
| 2018/0070880 A1 | 3/2018 | Trembly et al. |
| 2018/0074547 A1 | 3/2018 | Smadi et al. |
| 2018/0116877 A1 | 5/2018 | Ineichen |
| 2018/0132287 A1 | 5/2018 | Cheng et al. |
| 2018/0192514 A1 | 7/2018 | Seo |
| 2018/0200414 A1 | 7/2018 | Askem et al. |
| 2018/0206758 A1 | 7/2018 | Feldkamp et al. |
| 2018/0235484 A1 | 8/2018 | Mozdzierz |
| 2018/0296397 A1 | 10/2018 | Askem et al. |
| 2019/0021911 A1 | 1/2019 | Askem et al. |
| 2019/0060126 A1 | 2/2019 | Ribble et al. |
| 2019/0076298 A1 | 3/2019 | Quintanar et al. |
| 2019/0083025 A1 | 3/2019 | Aung et al. |
| 2019/0133812 A1 | 5/2019 | Seres et al. |
| 2019/0159938 A1 | 5/2019 | Askem et al. |
| 2019/0175098 A1 | 6/2019 | Burns |
| 2019/0192066 A1 | 6/2019 | Schoess et al. |
| 2019/0231939 A1 | 8/2019 | Askem et al. |
| 2019/0290496 A1 | 9/2019 | Brownhill et al. |
| 2019/0374387 A1 | 12/2019 | Ribble et al. |
| 2020/0054218 A1 | 2/2020 | Xi |
| 2020/0078482 A1 | 3/2020 | Yoon et al. |
| 2020/0078499 A1 | 3/2020 | Gadde et al. |
| 2020/0100711 A1 | 4/2020 | Choudhury et al. |
| 2020/0147407 A1 | 5/2020 | Efremkin |
| 2020/0281512 A1 | 9/2020 | Grubb et al. |
| 2020/0281513 A1 | 9/2020 | Grubb et al. |
| 2020/0281529 A1 | 9/2020 | Grubb et al. |
| 2020/0289346 A1 | 9/2020 | Hansen et al. |
| 2020/0330258 A1 | 10/2020 | Hansen et al. |
| 2020/0360547 A1 | 11/2020 | Smith et al. |
| 2021/0137446 A1 | 5/2021 | Brownhill et al. |
| 2021/0145359 A1 | 5/2021 | Hunt et al. |
| 2021/0212855 A1 | 7/2021 | Hansen et al. |
| 2022/0079814 A1 | 3/2022 | Chen et al. |

FOREIGN PATENT DOCUMENTS

| | | |
|---|---|---|
| CN | 106102322 A | 11/2016 |
| CN | 109350362 A | 2/2019 |
| DE | 102012211015 A1 | 1/2014 |
| DE | 102013013013 A1 | 2/2015 |
| EP | 2454990 A2 | 5/2012 |
| EP | 2565630 A1 | 3/2013 |
| EP | 3231478 A1 | 10/2017 |
| EP | 3409190 A1 | 12/2018 |
| EP | 3499510 A1 | 6/2019 |
| EP | 3837520 A1 | 6/2021 |
| GB | 1476894 A | 6/1977 |
| GB | 2316171 A | 2/1998 |
| GB | 2563602 A | 12/2018 |
| GB | 2614490 A | 7/2023 |
| JP | 2009225863 A | 10/2009 |
| KR | 20120119523 A | 10/2012 |
| KR | 101224629 B1 | 1/2013 |
| KR | 20140024743 A | 3/2014 |
| KR | 20140058041 A | 5/2014 |
| KR | 20160071044 A | 6/2016 |
| KR | 20190105898 A | 9/2019 |
| NL | 1027236 C2 | 4/2006 |
| WO | WO-0021433 A1 | 4/2000 |
| WO | WO-0043046 A2 | 7/2000 |
| WO | WO-02063260 A2 | 8/2002 |
| WO | WO-03067229 A1 | 8/2003 |
| WO | WO-2006041997 A2 | 4/2006 |
| WO | WO-2007030379 A2 | 3/2007 |
| WO | WO-2008006150 A1 | 1/2008 |
| WO | WO-2008010604 A1 | 1/2008 |
| WO | WO-2009052607 A1 | 4/2009 |
| WO | WO-2009120951 A2 | 10/2009 |
| WO | WO-2009141777 A1 | 11/2009 |
| WO | WO-2010020919 A1 | 2/2010 |
| WO | WO-2010105053 A2 | 9/2010 |
| WO | WO-2011082420 A1 | 7/2011 |
| WO | WO-2011123848 A1 | 10/2011 |
| WO | WO-2012141999 A1 | 10/2012 |
| WO | WO-2013026999 A1 | 2/2013 |
| WO | WO-2013044226 A1 | 3/2013 |
| WO | WO-2014036577 A1 | 3/2014 |
| WO | WO-2014116816 A1 | 7/2014 |
| WO | WO-2015112095 A1 | 7/2015 |
| WO | WO-2015168720 A1 | 11/2015 |
| WO | WO-2016025438 A1 | 2/2016 |
| WO | WO-2016030752 A1 | 3/2016 |
| WO | WO-2016058032 A1 | 4/2016 |
| WO | WO-2016073777 A1 | 5/2016 |
| WO | WO-2016100218 A1 | 6/2016 |
| WO | WO-2016110564 A1 | 7/2016 |
| WO | WO-2016136340 A1 | 9/2016 |
| WO | WO-2016187136 A1 | 11/2016 |
| WO | WO-2016205872 A1 | 12/2016 |
| WO | WO-2016205881 A1 | 12/2016 |
| WO | WO-2017021006 A1 | 2/2017 |
| WO | WO-2017021965 A2 | 2/2017 |
| WO | WO-2017033058 A1 | 3/2017 |
| WO | WO-2017037479 A1 | 3/2017 |
| WO | WO-2017041014 A1 | 3/2017 |
| WO | WO-2017041385 A1 | 3/2017 |
| WO | WO-2017041386 A1 | 3/2017 |
| WO | WO-2017041387 A1 | 3/2017 |
| WO | WO-2017119996 A1 | 7/2017 |
| WO | WO-2017205728 A1 | 11/2017 |
| WO | WO-2017214188 A1 | 12/2017 |
| WO | WO-2018035612 A1 | 3/2018 |
| WO | WO-2018060417 A1 | 4/2018 |
| WO | WO-2018064569 A1 | 4/2018 |
| WO | WO-2018115461 A1 | 6/2018 |
| WO | WO-2018144938 A1 | 8/2018 |
| WO | WO-2018144941 A1 | 8/2018 |
| WO | WO-2018144943 A1 | 8/2018 |
| WO | WO-2018144946 A1 | 8/2018 |
| WO | WO-2018185138 A1 | 10/2018 |
| WO | WO-2018189265 A1 | 10/2018 |
| WO | WO-2018209090 A1 | 11/2018 |
| WO | WO-2018211458 A1 | 11/2018 |
| WO | WO-2018234443 A1 | 12/2018 |
| WO | WO-2019020550 A2 | 1/2019 |
| WO | WO-2019020551 A1 | 1/2019 |
| WO | WO-2019020666 A1 | 1/2019 |
| WO | WO-2019030384 A2 | 2/2019 |
| WO | WO-2019048624 A1 | 3/2019 |
| WO | WO-2019048626 A1 | 3/2019 |
| WO | WO-2019048638 A1 | 3/2019 |
| WO | WO-2019063481 A1 | 4/2019 |
| WO | WO-2019063488 A2 | 4/2019 |
| WO | WO-2019067264 A1 | 4/2019 |
| WO | WO-2019072531 A1 | 4/2019 |
| WO | WO-2019076967 A2 | 4/2019 |
| WO | WO-2019096828 A1 | 5/2019 |
| WO | WO-2019140441 A2 | 7/2019 |
| WO | WO-2019140444 A1 | 7/2019 |
| WO | WO-2019140448 A1 | 7/2019 |
| WO | WO-2019140449 A1 | 7/2019 |
| WO | WO-2019193141 A1 | 10/2019 |
| WO | WO-2019216883 A1 | 11/2019 |
| WO | WO-2019230183 A1 | 12/2019 |
| WO | WO-2019238180 A1 | 12/2019 |
| WO | WO-2019238181 A1 | 12/2019 |
| WO | WO-2019238182 A1 | 12/2019 |
| WO | WO-2019238195 A1 | 12/2019 |
| WO | WO-2019238196 A1 | 12/2019 |

(56) References Cited

FOREIGN PATENT DOCUMENTS

| WO | WO-2019238197 A1 | 12/2019 |
|---|---|---|
| WO | WO-2019238198 A1 | 12/2019 |
| WO | WO-2020002416 A1 | 1/2020 |
| WO | WO-2020043806 A1 | 3/2020 |
| WO | WO-2020139541 A1 | 7/2020 |
| WO | WO-2020157103 A1 | 8/2020 |
| WO | WO-2020159677 A1 | 8/2020 |
| WO | WO-2020167547 A1 | 8/2020 |
| WO | WO-2020187851 A1 | 9/2020 |
| WO | WO-2020242876 A1 | 12/2020 |
| WO | WO-2021059209 A1 | 4/2021 |

OTHER PUBLICATIONS

Bandodkar A.J., et al., "Battery-Free, Skin-Interfaced Microfluidic/Electronic Systems for Simultaneous Electrochemical, Colorimetric and Volumetric Analysis of Sweat," Science Advances, vol. 5 (1), Jan. 18, 2019, retrieved from http://advances.sciencemag.org/content/5/1/eaav3294, 16 pages.

Cauwe M., et al., "Technology Development for a Low-Cost, Roll-to-Roll Chip Embedding Solution Based on PET Foils," 18th European Microelectronics and Packaging Conference (EMPC), IEEE, Sep. 12, 2011, 6 pages.

Farooqui M.F., et al., "Low Cost Inkjet Printed Smart Bandage for Wireless Monitoring of Chronic Wounds," Scientific Reports, vol. 6, Jun. 29, 2016, 14 pages.

Geng Y., et al., "A Hybrid Low Power Biopatch for Body Surface Potential Measurement," IEEE Journal of Biomedical and Health Informatics, vol. 17, No. 3, May 1, 2013, pp. 591-599.

George J., et al., "Reliability of Plastic-Encapsulated Electronic Components in Supersaturated Steam Environments," IEEE Transactions on Components, Packaging and Manufacturing Technology, vol. 5 (10), Oct. 2015, pp. 1423-1431.

Iannetta Jr. R.A., et al., "Successful Case Histories of Polymer Based Circuitry on Flexible Film Substrates," Electro/94 International Conference Proceedings Combined Volumes, IEEE, XP010149465, May 10-12, 1994, pp. 885-889.

International Search Report and Written Opinion for Application No. PCT/EP2020/057145, mailed Aug. 24, 2020.

Little Miss Plasters, kidstravelclub.co.uk., retrieved from http://www.kidstravelclub.co.uk/little-miss-girls-childrens-plasters on Aug. 26, 2016, 2 pages.

Lu B., et al., "A Study of the Autofluorescence of Parylene Materials for μTAS Applications," Lab on Chip, vol. 10 (14), Jul. 2010, pp. 1826-1834.

McLeod A.J., et al., "Motion Magnification for Endoscopic Surgery," Progress in Biomedical Optics and Imaging, SPIE—International Society for Optical Engineering, Mar. 12, 2014, vol. 9036, 8 pages.

Mehmood N., et al., "Applications Of Modern Sensors And Wireless Technology In Effective Wound Management: Modern Sensors And Wireless Technology," Journal of Biomedical Materials Research Part B, vol. 102, 2014, pp. 885-895.

Mostafalu P., et al., "Wireless Flexible Smart Bandage For Continuous Monitoring Of Wound Oxygenation," IEEE Transactions on Biomedical Circuits and Systems, vol. 9 (5), Oct. 2015, pp. 670-677 (8 pages).

Narusawa H., "The Corona Discharge Causes Short Destruction that had Bad Influence on a Power Switching Circuit," Adphox Corporation, Jan. 1, 2009, retrieved from http://www.adphox.co.jp/keisokuki/ke-english-corona/CORONA_DISCHARGE_EN.pdf, 12 pages.

Pang Q., et al., "Smart Flexible Electronics-Integrated Wound Dressing for Real-Time Monitoring and On-Demand Treatment of Infected Wounds," Advanced Science, vol. 7, Jan. 10, 2020, 1902673, 10 pages.

Raviglione A., et al., "Real-Time Smart Textile-Based System to Monitor Pressure Offloading of Diabetic Foot Ulcers," Journal of Diabetes Science and Technology, vol. 11 (5), Sep. 2017, pp. 894-898.

Rose D.P., et al., "Adhesive RFID Sensor Patch for Monitoring of Sweat Electrolytes," IEEE Transactions on Biomedical Engineering, vol. 62 (6), Jun. 2015, first published on Nov. 11, 2015, pp. 1457-1465.

Wakita J., et al., "Variations in Optical Absorption and Fluorescence Spectra for Polyimide Thin Films Caused by Structural Isomerism," Journal of Photopolymer Science and Technology, Jan. 1, 2003, 1 page.

Willis B., "Conformal Coating Inspection & Coating Faults," Vision Engineering, Jul. 21, 2016, retrieved from http://www.visioneng.com/wp-content/uploads/2017/11/Conformal-Coating-Inspection-and-Defects.21JUL16.pdf, 35 pages.

Willis B., "Guide to Conformal Coating & Cleaning Defects Contents," Mar. 1, 2014, retrieved from http://coatingguide.smartgroup.org/Files%20pdf/Coating%20Defects%20V2%2014March2014.pdf, vol. 1, 31 pages.

International Preliminary Report on Patentability for Application No. PCT/EP2020/057145, mailed on Sep. 30, 2021, 11 pages.

\* cited by examiner

RULES FOR SENSOR INTEGRATED SUBSTRATES

CROSS-REFERENCE TO RELATED APPLICATIONS

This application is a U.S. national stage application of International Patent Application No. PCT/EP2020/057145, filed Mar. 16, 2020, which claims priority to U.K. Provisional Application No. GB 1903661.5, filed on Mar. 18, 2019, entitled "DESIGN RULES FOR SENSOR INTEGRATED SUBSTRATES", and also claims priority to U.K. Provisional Application No. GB1918640.2, filed Dec. 17, 2019, entitled "MULTILAYER FLEXIBLE SUBSTRATE FOR SENSOR INTEGRATED DRESSINGS AND SYSTEMS", the disclosure of which is hereby incorporated by reference in its entirety.

TECHNICAL FIELD

Embodiments of the present disclosure relate to sensor integrated substrates, which can be incorporated into wound dressings and systems, and in particular to design rules for such substrates.

DESCRIPTION OF THE RELATED ART

Nearly all areas of medicine may benefit from improved information regarding the state of the tissue, organ, or system to be treated, particularly if such information is gathered in real-time during treatment. Many types of treatments are still routinely performed without the use of sensor data collection; instead, such treatments rely upon visual inspection by a caregiver or other limited means rather than quantitative sensor data. For example, in the case of wound treatment via dressings and/or negative pressure wound therapy, data collection is generally limited to visual inspection by a caregiver and often the underlying wounded tissue may be obscured by bandages or other visual impediments. Even intact, unwounded skin may have underlying damage that is not visible to the naked eye, such as a compromised vascular or deeper tissue damage that may lead to an ulcer. Similar to wound treatment, during orthopedic treatments requiring the immobilization of a limb with a cast or other encasement, only limited information is gathered on the underlying tissue. In instances of internal tissue repair, such as a bone plate, continued direct sensor-driven data collection is not performed. Further, braces and/or sleeves used to support musculoskeletal function do not monitor the functions of the underlying muscles or the movement of the limbs. Outside of direct treatments, common hospital room items such as beds and blankets could be improved by adding capability to monitor patient parameters.

Such wound monitoring and/or treatment systems present unique problems due to being in contact with tissue. In addition, a wound should be allowed to heal without impediment. At the same time, care must be taken to ensure that such systems are reliable and safe for use on human or animal tissue.

Therefore, there is a need for improved wound monitoring and/or treatment systems.

SUMMARY

In some cases, a method of manufacturing a wound monitoring and/or therapy apparatus (such as, a wound dressing) can include positioning on a substantially flexible substrate a first conductive track configured to be connected to a first sensor, the first track having a first minimum width to maintain integrity of an electrical signal conducted by the first conductive track, positioning on the substrate a second conductive track configured to be connected to a second sensor, the second track having a second minimum width to maintain integrity of an electrical signal conducted by the second conductive track, and positioning on the substrate a third track configured to be connected to a third sensor, the third track having a third minimum width to maintain integrity of an electrical signal conducted by the first conductive track. The first, second, and third conductive tracks can be positioned on portions of the substrate that are not configured to be perforated with a plurality of openings, the plurality of openings configured to allow fluid to pass through the substrate. At least one of locations or sizes of the plurality of openings configured to allow fluid to pass through the substrate can constrain a maximum dimension at least one of the first, second, or third minimum widths. The first, second, and third sensors can be sensors of different types.

The method of the preceding paragraph and/or any of the methods described herein can include one or more of the following features. The method can include perforating the substrate to form the plurality of openings. Perforating the substrate to form the plurality of openings can include not perforating the portions of the substrate on which the first, second, and third conductive tracks are positioned. Positioning at least one of the first, second, or third conductive tracks can include printing the at least one of the first, second, or third conductive tracks using conductive ink. Conductive ink can include silver ink. The method can include positioning on the substrate a fourth track configured to provide power to at least one of the first, second, or third sensors, the fourth track having a fourth minimum width, wherein at least one of the locations or sizes of the plurality of openings can further constrain a maximum dimension of the fourth minimum width. The first, second, and third conductive tracks, first sensor, second sensor, and third sensor can be positioned at least a minimum distance away from the plurality of openings.

The method of any of the preceding paragraphs and/or any of the methods described herein can include one or more of the following features. At least two of the first, second, or third minimum widths can be different from one another. The first conductive track can be configured to conduct an analog signal, the second conductive track can be configured to conduct a digital signal, and the first minimum width can be smaller than the second minimum width. The first sensor can be a temperature sensor, the second sensor can be a light sensor, and the third sensor can be an impedance sensor.

In some cases, a method of manufacturing a wound monitoring and/or therapy apparatus (such as, a wound dressing) can include positioning on a substantially flexible substrate a first conductive track oriented in a first direction and configured to transmit electrical signals and positioning on the substrate adjacent to the first conductive track at a first minimum distance from the first conductive track a second conductive track, the second conductive track oriented in the first direction and configured to transmit electrical signals. The first minimum distance can be defined by at least one of a location or size of at least one opening configured to allow exudate to pass through the substrate.

The method of any of preceding paragraphs and/or any of the methods described herein can include one or more of the following features. The method can include perforating the substrate to form the at least one opening in a portion of the substrate separating the first conductive track from the second conductive track. The method can include positioning on the substrate a third conductive track oriented in a second direction and configured to transmit electrical signals, the second direction different from the first direction and positioning on the substrate adjacent to the conductive third track at a second minimum distance from the third conductive track a fourth conductive track, the fourth conductive track oriented in the second direction and configured transmit electrical signals, the second minimum distance being different than the first minimum distance. Positioning on the substrate third and fourth conductive tracks oriented in the second direction can include positioning third and fourth conductive tracks at a third minimum distance from each of the first and second conductive tracks oriented in the first direction. The second direction can be perpendicular to the first direction. Positioning at least one of the first, second, third, or fourth conductive tracks can include printing the at least one of the first, second, third, or fourth conductive tracks using conductive ink. Conductive ink can include silver ink.

In some cases, a method of manufacturing a wound monitoring and/or therapy apparatus (such as, a wound dressing) can include positioning on a substantially flexible substrate a first conductive track oriented in a first direction and configured to transmit electrical signals, positioning on the substrate a second conductive track oriented in a second direction different from the first direction, the second conductive track configured to transmit electrical signals, the second conductive track having same width as the first conductive track, and forming an electrical connection between the first and second conductive tracks by forming a substantially circular conductive area overlapping the first and second conductive tracks, a radius of the conductive area being about one half of the width of the first and conductive second tracks.

The method of any of preceding paragraphs and/or any of the methods described herein can include one or more of the following features. Positioning at least one of the first or second conductive tracks can include printing the at least one of the first or second conductive tracks using conductive ink. Conductive ink can include silver ink. Forming the electrical connection can include removing at least a portion of dry ink to form the substantially circular conductive area with the radius of about one half of the width of the first and second conductive tracks.

In some cases, a method of manufacturing a wound monitoring and/or therapy apparatus (such as, a wound dressing) can include positioning on a substantially flexible substrate a first conductive track configured to transmit electrical signals, the first conductive track having a first width, positioning on the substrate a second conductive track configured to transmit electrical signals, the second conductive track having a second width different than the first width, and electrically connecting first and second tracks with a curved connector.

The method of any of preceding paragraphs and/or any of the methods described herein can include one or more of the following features. Portions of the first conductive track proximal to the connector and of the second conductive track proximal to the connector can be shaped to not include any transitions of approximately 90 degrees. At least one of positioning at least one of the first or second conductive tracks or electrically connecting first and second tracks with the curved connector can include printing the at least one of the first conductive track, second conductive track, or the curved connector using conductive ink. Conductive ink can include silver ink.

In some cases, a method of manufacturing a wound monitoring and/or therapy apparatus (such as, a wound dressing) can include positioning on a flexible substrate a first conductive track oriented in a first direction and configured to transmit electrical signals; positioning on the flexible substrate a second conductive track oriented in a second direction different from the first direction, the second conductive track configured to transmit electrical signals, at least a portion of the second conductive track overlapping at least a portion of the first conductive track and forming a mask region between the portion of the first conductive track overlapping the portion of the second conductive track, the mask region electrically isolating the overlapping portions of the first and second conductive tracks. Positioning at least one of the first or second conductive tracks can include printing the at least one of the first or second conductive tracks using conductive ink. The mask region can be formed from non-conducive paint.

A wound dressing can include a flexible or substantially flexible substrate with a first side and a second side opposite the first side. A first electrically conductive track can be positioned on the first side of the substrate. A second electrically conductive track can be positioned on the second side of the substrate. The second electrically conductive track can be electrically connected to the first electrically conductive track via an electrically conductive material that passes through the substrate.

The wound dressing of any preceding paragraphs and/or any of the wound dressings disclosed herein can include one or more of the following features. The electrically conductive material is positioned in a perforation through the substrate. The wound dressing can include a first electronic component positioned on the first side of the substrate and electrically connected to the first electrically conductive track. The wound dressing can include a second electronic component positioned on the second side of the substrate and electrically connected to the second electrically conductive track. The first electronic component can include a plurality of sensors configured to measure a plurality of parameters of a wound. The second electronic component can include an antenna configured to transmit at least some of the plurality of parameters measured by the plurality of sensors to a remote computing device.

The wound dressing of any preceding paragraphs and/or any of the wound dressings disclosed herein can include one or more of the following features. The wound dressing can include a substantially non-stretchable coating applied to at least one of the first electronic component, second electronic component, first electrically conductive track, or second electrically conductive track. The wound dressing can include a substantially stretchable coating applied over the substantially non-stretchable coating. The substrate can include or be made of thermoplastic polyurethane (TPU). A portion of the first electrically conductive track can overlap a portion of the second electrically conductive track. At least one of the first or second electrically conductive tracks can cover at least part of the perforation. First and second electrically conductive tracks can include conductive ink or conductive glue. The electrically conductive material can include conductive ink or conductive glue. Conductive ink can include silver ink. First electrically conductive track may not directly contact the second electrically conductive track.

The wound dressing of any preceding paragraphs and/or any of the wound dressings disclosed herein can include one or more of the following features. The wound dressing can include a third electrically conductive track positioned on the first side of the substrate. The wound dressing can include a first non-conductive mask separating the first and third electrically conductive tracks. The wound dressing can include a fourth electrically conductive track positioned on the second side of the substrate. The wound dressing can include a second non-conductive mask separating the second and fourth electrically conductive tracks.

A method of manufacturing a wound dressing can include passing an electrically conductive material through a flexible or substantially flexible substrate of the wound dressing. The method can include positioning a first electrically conductive track on a first side of the substrate. The method can include forming an electrical connection with the electrically conductive material. The method can include positioning a second electrically conductive track on a second side of the substrate located opposite the first side. The method can include forming an electrical connection with the electrically conductive material. The first and second electrically conductive tracks can be electrically connected via the conductive material.

The method of any preceding paragraphs and/or any of the methods disclosed herein can include one or more of the following features. The method can include forming a perforation through the substrate and at least partially filling the perforation with the electrically conductive material. The method can include positioning a first electronic component on the first side of the substrate and electrically connecting the first electronic component to the first electrically conductive track. The method can include positioning a second electronic on the second side of the substrate and electrically connecting the second electronic component to the second electrically conductive track.

The method of any preceding paragraphs and/or any of the methods disclosed herein can include one or more of the following features. The method can include applying a substantially non-stretchable coating to at least one of the first electronic component, second electronic component, first electrically conductive track, or second electrically conductive track. The method can include applying a substantially stretchable coating over the substantially non-stretchable coating. The substrate can include or be made of thermoplastic polyurethane (TPU). Positioning the second electrically conductive track on the second side of the substrate can include overlapping a portion of the first electrically conductive track. Positioning at least one of the first or second electrically conductive tracks can include covering at least part of the perforation. Positioning at least one of the first or second electrically conductive tracks can include printing the at least one of the first or second electrically conductive tracks using conductive ink or conductive glue. Electrically conductive material can include conductive ink or conductive glue. Conductive ink can include silver ink.

The method of any preceding paragraphs and/or any of the methods disclosed herein can include one or more of the following features. The method can include positioning a third electrically conductive track on the first side of the substrate. The method can include positioning a first non-conductive mask between the first and third electrically conductive tracks. The method can include positioning a fourth electrically conductive track on the second side of the substrate. The method can include positioning a second non-conductive mask between the second and fourth electrically conductive tracks.

A method of manufacturing a wound monitoring and/or therapy apparatus (such as, a wound dressing) can include positioning on a substantially flexible substrate a first conductive track oriented in a first direction and configured to transmit electrical signals. The method can include positioning on the substrate a first non-conductive mask by covering the first conductive track with the first mask except for a portion of the first conductive track configured to be electrically connected to another conductive track or an electrical component. Covering the first conductive track with the first mask can prevent or reduce migration or dispersal of conductive material of the first conductive track.

The method of any of preceding paragraphs and/or any of the methods described herein can include one or more of the following features. Positioning the first conductive track can include printing the first conductive track on the substrate using conductive ink or conductive glue. The portion of the first conductive track can be a pad or a via. Positioning on the substrate the first mask can include covering substantially entire surface of the substrate with the first mask.

The method of any of preceding paragraphs and/or any of the methods described herein can include one or more of the following features. The method can include positioning on the substrate a second conductive track oriented in a second direction different from the first direction, the second conductive track configured to transmit electrical signals. The method can include positioning on the substrate a second non-conductive mask by covering the second conductive track with the second mask except for a portion of the second conductive track configured to be electrically connected to another conductive track or an electrical component. Covering the second conductive track with the second mask can prevent or reduce migration or dispersal of conductive material of the second conductive track. Positioning the second conductive track can include printing the second conductive track on the substrate using conductive ink or conductive glue. The portion of the second conductive track can be a pad or a via. Positioning on the substrate the second mask can include covering substantially entire surface of the substrate with the second mask.

Any of the features of any of the methods described herein can be used with any of the features of any of the other methods described herein.

In some cases, a wound monitoring and/or therapy apparatus (such as a wound dressing) manufactured using the methods of any one or more of preceding paragraphs and/or any of the methods described herein is disclosed. In some cases, a substrate supporting one or more electronic components and/or connections manufactured using the methods of any one or more of preceding paragraphs and/or any of the methods described herein is disclosed.

BRIEF DESCRIPTION OF THE DRAWINGS

Embodiments of the present disclosure will now be described hereinafter, by way of example only, with reference to the accompanying drawings in which:

FIGS. 1B-1D illustrate substrates supporting electronic components, in which FIG. 1B illustrates a perspective view of a substrate supporting electronic components and FIGS. 1C-1D illustrate perspective and top views of a perforated substrate supporting electronic components;

DETAILED DESCRIPTION

Figure 1A:
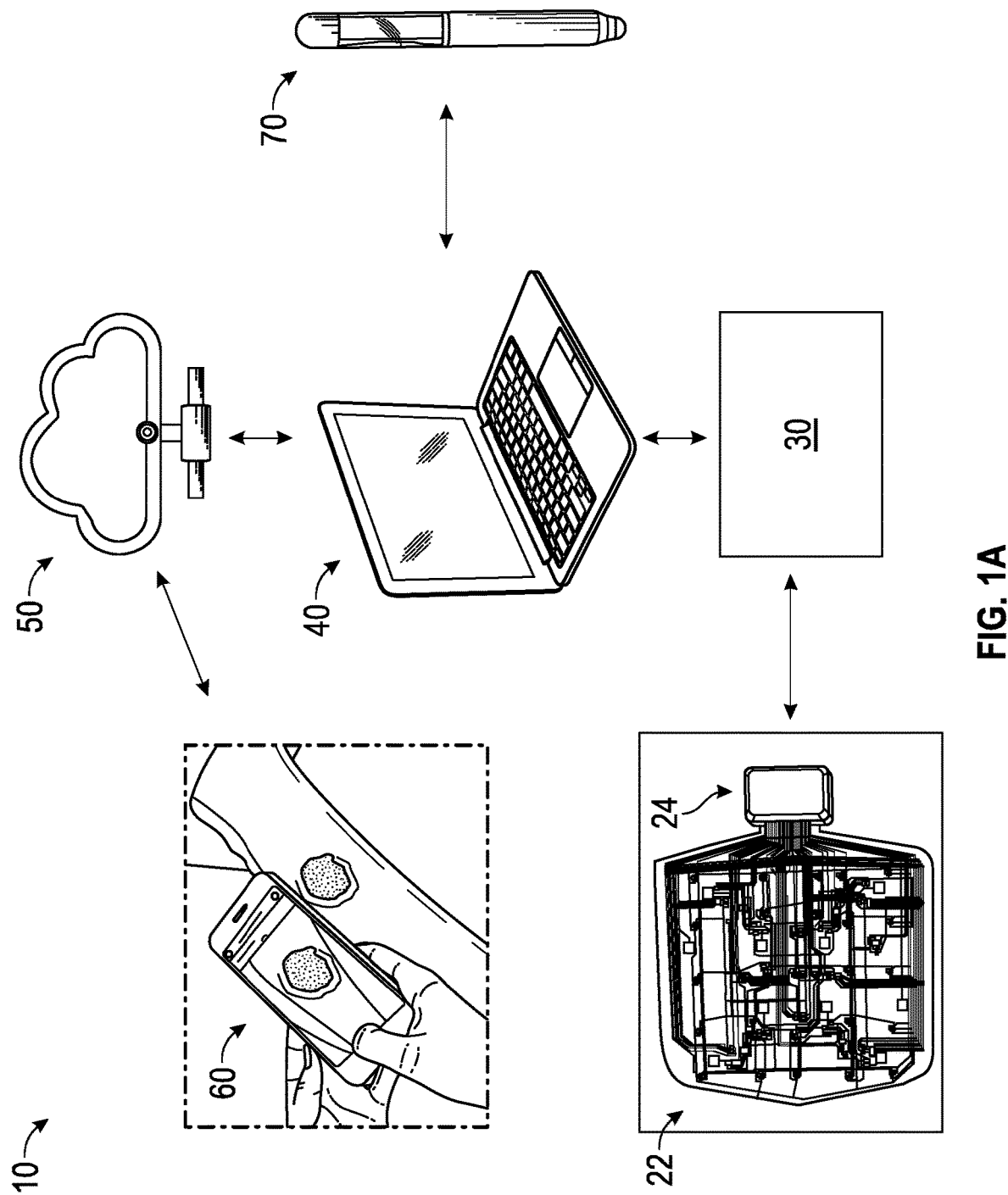
FIG. 1A illustrates a wound monitoring and therapy system.

Embodiments disclosed herein relate to apparatuses and methods of at least one of monitoring or treating biological tissue with sensor-enabled substrates. The embodiments disclosed herein are not limited to treatment or monitoring of a particular type of tissue or injury, instead the sensor-enabled technologies disclosed herein are broadly applicable to any type of therapy that may benefit from sensor-enabled substrates. Some implementations utilize sensors and data collection relied upon by health care providers to make both diagnostic and patient management decisions.

Some embodiments disclosed herein relate to the use of sensors mounted on or embedded within substrates configured to be used in the treatment of both intact and damaged human or animal tissue. Such sensors may collect information about the surrounding tissue and transmit such information to a computing device or a caregiver to be utilized in further treatment. In certain embodiments, such sensors may be attached to the skin anywhere on the body, including areas for monitoring arthritis, temperature, or other areas that may be prone to problems and require monitoring. Sensors disclosed herein may also incorporate markers, such as radiopaque markers, to indicate the presence of the device, for example prior to performing an MRI or other technique.

The sensor embodiments disclosed herein may be used in combination with clothing. Non-limiting examples of clothing for use with embodiments of the sensors disclosed herein include shirts, pants, trousers, dresses, undergarments, outer-garments, gloves, shoes, hats, and other suitable garments. In certain embodiments, the sensor embodiments disclosed herein may be welded into or laminated into/onto the particular garments. The sensor embodiments may be printed directly onto the garment and/or embedded into the fabric. Breathable and printable materials such as microporous membranes may also be suitable.

Sensor embodiments disclosed herein may be incorporated into cushioning or bed padding, such as within a hospital bed, to monitor patient characteristics, such as any characteristic disclosed herein. In certain embodiments, a disposable film containing such sensors could be placed over the hospital bedding and removed/replaced as needed.

In some implementations, the sensor embodiments disclosed herein may incorporate energy harvesting, such that the sensor embodiments are self-sustaining. For example, energy may be harvested from thermal energy sources, kinetic energy sources, chemical gradients, or any suitable energy source.

The sensor embodiments disclosed herein may be utilized in rehabilitation devices and treatments, including sports medicine. For example, the sensor embodiments disclosed herein may be used in braces, sleeves, wraps, supports, and other suitable items. Similarly, the sensor embodiments disclosed herein may be incorporated into sporting equipment, such as helmets, sleeves, and/or pads. For example, such sensor embodiments may be incorporated into a protective helmet to monitor characteristics such as acceleration, which may be useful in concussion diagnosis.

The sensor embodiments disclosed herein may be used in coordination with surgical devices, for example, the NAVIO surgical system by Smith & Nephew Inc. In some implementations, the sensor embodiments disclosed herein may be in communication with such surgical devices to guide placement of the surgical devices. In some implementations, the sensor embodiments disclosed herein may monitor blood flow to or away from the potential surgical site or ensure that there is no blood flow to a surgical site. Further surgical data may be collected to aid in the prevention of scarring and monitor areas away from the impacted area.

To further aid in surgical techniques, the sensors disclosed herein may be incorporated into a surgical drape to provide information regarding tissue under the drape that may not be immediately visible to the naked eye. For example, a sensor embedded flexible drape may have sensors positioned advantageously to provide improved area-focused data collection. In certain implementations, the sensor embodiments disclosed herein may be incorporated into the border or interior of a drape to create fencing to limit/control the surgical theater.

Sensor embodiments as disclosed herein may also be utilized for pre-surgical assessment. For example, such sensor embodiments may be used to collect information about a potential surgical site, such as by monitoring skin and the underlying tissues for a possible incision site. For example, perfusion levels or other suitable characteristics may be monitored at the surface of the skin and deeper in the tissue to assess whether an individual patient may be at risk for surgical complications. Sensor embodiments such as those disclosed herein may be used to evaluate the presence of microbial infection and provide an indication for the use of antimicrobials. Further, sensor embodiments disclosed herein may collect further information in deeper tissue, such as identifying pressure ulcer damage and/or the fatty tissue levels.

The sensor embodiments disclosed herein may be utilized in cardiovascular monitoring. For example, such sensor embodiments may be incorporated into a flexible cardiovascular monitor that may be placed against the skin to monitor characteristics of the cardiovascular system and communicate such information to another device and/or a caregiver. For example, such a device may monitor pulse rate, oxygenation of the blood, and/or electrical activity of the heart. Similarly, the sensor embodiments disclosed herein may be utilized for neurophysiological applications, such as monitoring electrical activity of neurons.

The sensor embodiments disclosed herein may be incorporated into implantable devices, such as implantable orthopedic implants, including flexible implants. Such sensor embodiments may be configured to collect information regarding the implant site and transmit this information to an external source. In some embodiments, an internal source may also provide power for such an implant.

The sensor embodiments disclosed herein may also be utilized for monitoring biochemical activity on the surface of the skin or below the surface of the skin, such as lactose buildup in muscle or sweat production on the surface of the skin. In some embodiments, other characteristics may be monitored, such as glucose concentration, urine concentration, tissue pressure, skin temperature, skin surface conductivity, skin surface resistivity, skin hydration, skin maceration, and/or skin ripping.

Sensor embodiments as disclosed herein may be incorporated into Ear, Nose, and Throat (ENT) applications. For example, such sensor embodiments may be utilized to monitor recovery from ENT-related surgery, such as wound monitoring within the sinus passage.

Sensor embodiments disclosed herein may encompass sensor printing technology with encapsulation, such as encapsulation with a polymer film. Such a film may be constructed using any polymer described herein, such as polyurethane. Encapsulation of the sensor embodiments may provide waterproofing of the electronics and protection from local tissue, local fluids, and other sources of potential damage.

In certain embodiments, the sensors disclosed herein may be incorporated into an organ protection layer. Such a sensor-embedded organ protection layer may both protect the organ of interest and confirm that the organ protection layer is in position and providing protection. Further, a sensor-embedded organ protection layer may be utilized to monitor the underlying organ, such as by monitoring blood flow, oxygenation, and other suitable markers of organ health. In some embodiments, a sensor-enabled organ protection layer may be used to monitor a transplanted organ, such as by monitoring the fat and muscle content of the organ. Further, sensor-enabled organ protection layers may be used to monitor an organ during and after transplant, such as during rehabilitation of the organ.

The sensor embodiments disclosed herein may be incorporated into treatments for wounds (disclosed in greater detail below) or in a variety of other applications. Non-limiting examples of additional applications for the sensor embodiments disclosed herein include: monitoring and treatment of intact skin, cardiovascular applications such as monitoring blood flow, orthopedic applications such as monitoring limb movement and bone repair, neurophysiological applications such as monitoring electrical impulses, and any other tissue, organ, system, or condition that may benefit from improved sensor-enabled monitoring.

Wound Therapy

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein) wound with or without reduced pressure, including for example a source of negative pressure and wound dressing components and apparatuses. The apparatuses and components comprising the wound overlay and packing materials or internal layers, if any, are sometimes collectively referred to herein as dressings. In some embodiments, the wound dressing can be provided to be utilized without reduced pressure.

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein).

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno-compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

Wound may also include tissue at risk of becoming a wound as discussed herein. For example, tissue at risk may include tissue over a bony protuberance (at risk of deep tissue injury/insult) or pre-surgical tissue (for example, knee tissue) that may has the potential to be cut (for example, for joint replacement/surgical alteration/reconstruction).

Some embodiments relate to methods of treating a wound with the technology disclosed herein in conjunction with one or more of the following: advanced footwear, turning a patient, offloading (such as, offloading diabetic foot ulcers), treatment of infection, systemix, antimicrobial, antibiotics, surgery, removal of tissue, affecting blood flow, physiotherapy, exercise, bathing, nutrition, hydration, nerve stimulation, ultrasound, electrostimulation, oxygen therapy, microwave therapy, active agents ozone, antibiotics, antimicrobials, or the like.

Alternatively or additionally, a wound may be treated using topical negative pressure (TNP) and/or traditional advanced wound care, which is not aided by the using of applied negative pressure (may also be referred to as non-negative pressure therapy).

Advanced wound care may include use of an absorbent dressing, an occlusive dressing, use of an antimicrobial and/or debriding agents in a wound dressing or adjunct, a pad (for example, a cushioning or compressive therapy, such as stockings or bandages), or the like.

In some embodiments, a wound dressing comprises one or more absorbent layer(s). The absorbent layer may be a foam or a superabsorbent.

In some embodiments, the disclosed technology may be used in conjunction with a non-negative pressure dressing. A non-negative pressure wound dressing suitable for providing protection at a wound site may comprise an absorbent layer for absorbing wound exudate and an obscuring element for at least partially obscuring a view of wound exudate absorbed by the absorbent layer in use. The obscuring element may be partially translucent. The obscuring element may be a masking layer.

In some embodiments, the non-negative pressure wound dressing as disclosed herein comprises the wound contact layer and the absorbent layer overlies the wound contact layer. The wound contact layer can carry an adhesive portion for forming a substantially fluid tight seal over the wound.

In some embodiments, the wound dressing as disclosed herein further comprises layer of a superabsorbent fiber, or a viscose fiber or a polyester fiber.

In some embodiments, the wound dressing as disclosed herein further comprises a backing layer. The backing layer may be a transparent or opaque film. Typically the backing layer comprises a polyurethane film (typically a transparent polyurethane film).

In some cases, the foam may be an open cell foam, or closed cell foam, typically an open cell foam. The foam can be hydrophilic.

The wound dressing may comprise a transmission layer and the layer can be foam. The transmission layer may be a polyurethane foam laminated to a polyurethane film.

The non-negative pressure wound dressing may be a compression bandage. Compression bandages are known for use in the treatment of oedema and other venous and lymphatic disorders, e.g., of the lower limbs. The compression bandage in some embodiments may comprise a bandage system comprising an inner skin facing layer and an elastic outer layer, the inner layer comprising a first ply of foam and a second ply of an absorbent nonwoven web, the inner layer and outer layer being sufficiently elongated so as to be capable of being wound about a patient's limb.

Negative Pressure Wound Therapy

In some embodiments, treatment of wounds can be performed using negative pressure wound therapy. It will be understood that embodiments of the present disclosure are generally applicable to use in TNP systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

Negative pressure therapy can be used for the treatment of open or chronic wounds that are too large to spontaneously close or otherwise fail to heal by means of applying negative pressure to the site of the wound. Topical negative pressure (TNP) therapy or negative pressure wound therapy (NPWT) involves placing a cover that is impermeable or semipermeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines or bacteria.

Some of the dressings used in NPWT can include many different types of materials and layers, for example, gauze, pads, foam pads or multi-layer wound dressings. One example of a multi-layer wound dressing is the PICO dressing, available from Smith & Nephew, includes a wound contact layer and a superabsorbent layer beneath a backing layer to provide a canister-less system for treating a wound with NPWT. The wound dressing may be sealed to a suction port providing connection to a length of tubing, which may be used to pump fluid out of the dressing or to transmit negative pressure from a pump to the wound dressing. Additionally, RENASYS-F, RENASYS-G, RENASYS-AB, and RENASYS-F/AB, available from Smith & Nephew, are additional examples of NPWT wound dressings and systems. Another example of a multi-layer wound dressing is the ALLEVYN Life dressing, available from Smith & Nephew, which includes a moist wound environment dressing that is used to treat the wound without the use of negative pressure.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (such as, −40 mmHg is less than −60 mmHg). Negative pressure that is "more" or "greater" than −X mmHg corresponds to pressure that is further from atmospheric pressure (such as, −80 mmHg is more than −60 mmHg). In some embodiments, local ambient atmospheric pressure is used as a reference point, and such local atmospheric pressure may not necessarily be, for example, 760 mmHg.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, or in synchronization with one or more physiological indices (such as, heartbeat).

Any of the embodiments disclosed herein can be used in combination with any of the features disclosed in one or more of WO2010/061225, US2016/114074, US2006/0142560, and U.S. Pat. No. 5,703,225, which describe absorbent materials; WO2013/007973, which describes non-negative pressure wound dressings; GB1618298.2 (filed on 28 Oct. 2016), GB1621057.7 (filed on 12 Dec. 2016), and GB1709987.0 (filed on 22 Jun. 2017), which describe multi-layered wound dressings; EP2498829 and EP1718257, which describe wound dressings; WO2006/110527, U.S.

Pat. No. 6,759,566, and US2002/0099318, which describe compression bandages; U.S. Pat. Nos. 8,235,955 and 7,753, 894, which describe wound closure devices; WO2013/ 175306, WO2016/174048, US2015/0190286, US2011/ 0282309, and US2016/0339158, which describe negative pressure wound therapy dressings, wound dressing components, wound treatment apparatuses, and methods. The disclosure of each of these applications is hereby incorporated by reference in its entirety.

Sensor Enabled Wound Monitoring and Therapy System

FIG. 1A illustrates a wound monitoring and therapy system 10 according to some embodiments. The system includes a sensor enabled wound dressing 22 connected to a controller 24. As is described herein, the dressing 22 can be placed on or in a wound of a patient and can utilize various sensors embedded or otherwise placed in the dressing 22 to collect measurement data from one or more of the wound or areas surrounding the wound, such as the periwound (which can include intact skin). The controller 24 can receive, store, and process data collected by the dressing 22. To facilitate communication, the dressing 22 can include one or more communication modules, such as one or more antennas as described herein. In some cases, the controller 24 can transmit one or more of commands and data to the dressing 22.

In some embodiments, wound dressing 22 can be disposable and controller 24 can be reusable. In some embodiments, wound dressing 22 can be reusable. In some embodiments, wound dressing 22 can be re-sterilized or otherwise sanitized or disinfected. In some embodiments, controller 24 can be disposable. In some embodiments, wound dressing 22 and controller 24 can be permanently connected and the combined wound dressing and control box be disposable, or reusable or re-sterilized or otherwise sanitized or disinfected. The controller 24 can be positioned on the wound dressing 22. The controller 24 can be spatially separated from the wound dressing 22, such as by a cable or another wired or wireless electrical connection. The controller 24 can include a power source (such as a battery), one or more processors, one or more data storage elements, and a communication device. In some embodiments, the controller 24 can include one or more sensors, such as a temperature sensor or light (or optical) sensor to gather information on patient or environmental conditions located away from the wound dressing 22. In some embodiments, the one or more sensors of the controller 24 can include an accelerometer, motion sensor or gyroscope.

In some embodiments, the wound dressing 22 can include one or more indicators to communicate information to a user. The indicators can be visual, audible, haptic, or tactile. Communicated information can include measurement data, wound status, or the like.

The controller 24 can communicate data to a communication device 30 as requested, periodically, or the like. Communication can be performed over a wired or wireless interface, such as via near field communication (NFC), RFID, or the like when the communication device is placed in communication range. For example, communication range can be close proximity, such as within approximately 3 cm or less or more, to the controller 24. Communication device 30 can be placed in communication range by a clinician, such as during initialization and at the end of treatment. The controller 24 can respond with data to a command from the communication device 30 requesting data. Communication can be performed via transfer of hardware or data storage, such as one or more memory storage devices (for example, SD card). In some cases, communication can be performed non-electronically, such as visually, audibly, or tactilely, and one or more of the controller 24 or communication device 30 can provide an interface for such non-electronic communication of data.

The communication device 30 can be connected via a wired or wireless interface to a computing device 40, such as a personal computer, tablet, smartphone, or the like. For example, wired USB protocol can be used for communication of data between devices 30 and 40. As another example, communication of data can be performed via transfer of hardware or data storage, such as one or more memory storage devices (for example, SD card). In some cases, communication of data can be performed non-electronically, such as visually, audibly, or tactilely, and one or more of the communication device 30 or computing device 40 can provide an interface for such non-electronic communication of data.

Computing device 40 can further process data collected by the dressing 22. For example, the computing device 40 can aggregate data collected from the dressing 22 and perfusion determination device 70, which is configured to determine skin perfusion pressure and communicate data to the computing device 40 via a wired or wireless interface. For example, wired USB protocol can be used for communication between devices 70 and 40.

Computing device 40 can be configured to communicate via a wired or wireless interface with a remote computing device 50 that stores and processes medical data. In some embodiments, remote computing device 50 can be a cloud computing device, which includes one or more of remote storage, server, processing device, or any means of information storage. For example, remote computing device 50 can process and store medical data according with one or more applicable security and privacy standards, such as Health Insurance Portability & Accountability Act (HIPAA), European Union's Directive on Data Protection, or the like. Remote computing device 50 can make data provided by one or more of the computing device 40 or the mobile device 60 available for remote accessing and viewing, such as on a mobile device 60. In certain implementations, additional data can be added for storage on the remote computing device 50. For example, additional data can be added by the mobile device 60 via a dedicated app, web browser interface, or the like. The remote computing device 50 can process the data from one or more of the wound dressing 22, perfusion determination device 70, or the mobile device and assess or determine treatment plan, such as suggest or adjust one or more treatment therapies.

As described herein, mobile device 60 can take one or more images of a patient's wound. Such data can be transmitted via wired or wireless interface to the remote computing device 50. Although a smartphone is illustrated, mobile device 60 can be any suitable computing device that includes imaging functionality, such as a camera. Mobile device 60 can also collect additional data, such as data input by a healthcare provider in response to a questionnaire.

Sensor Enabled Substrates and Wound Dressings

A wound dressing that incorporates a number of electronic components, including one or more sensors, can be utilized in order to monitor characteristics of a wound. Collecting and analyzing data from a wound can provide useful insights towards determining whether a wound is on a healing trajectory, selecting proper therapy, determining whether the wound has healed, or the like.

Figure 1B:
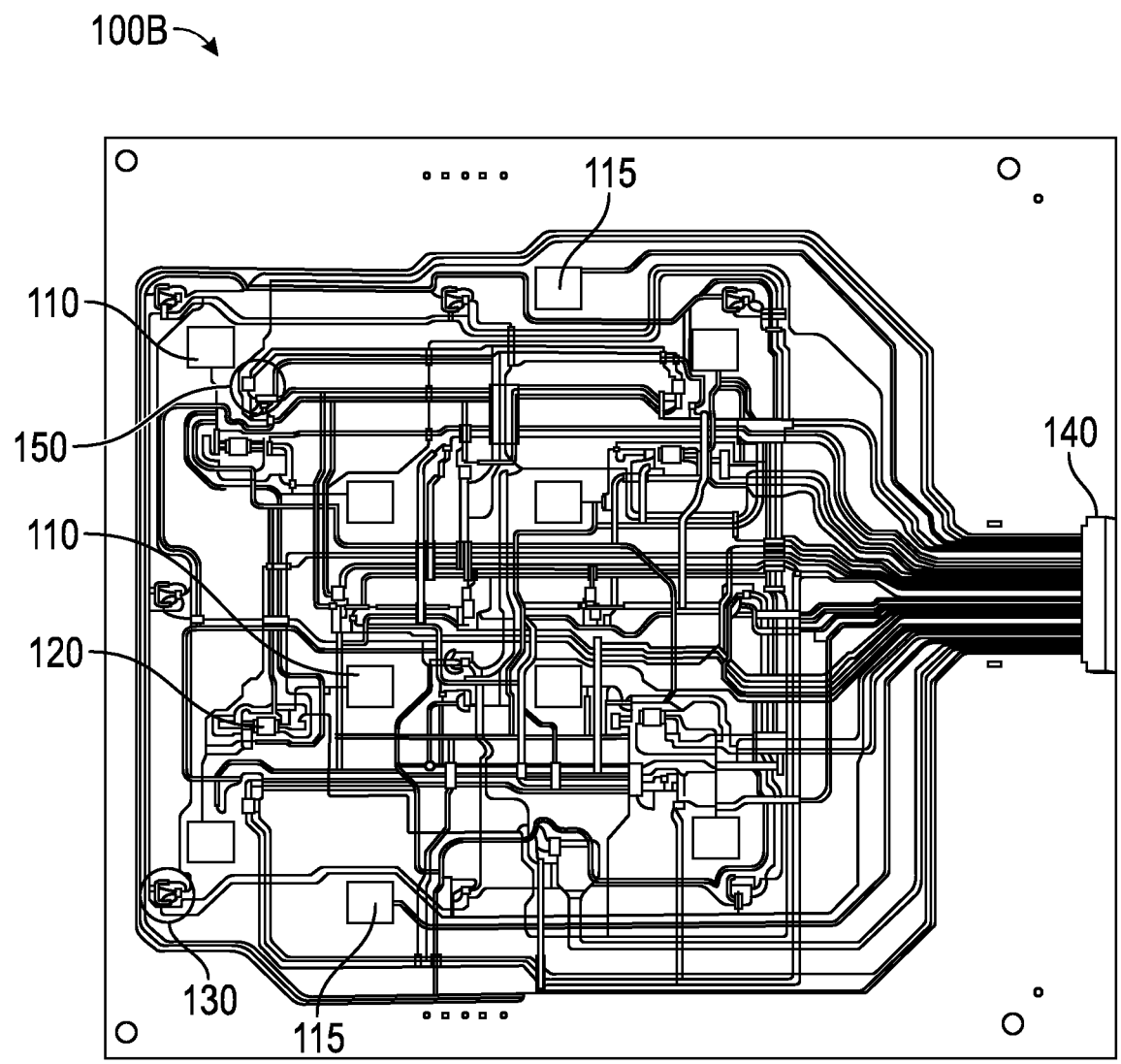
Figure 1C:
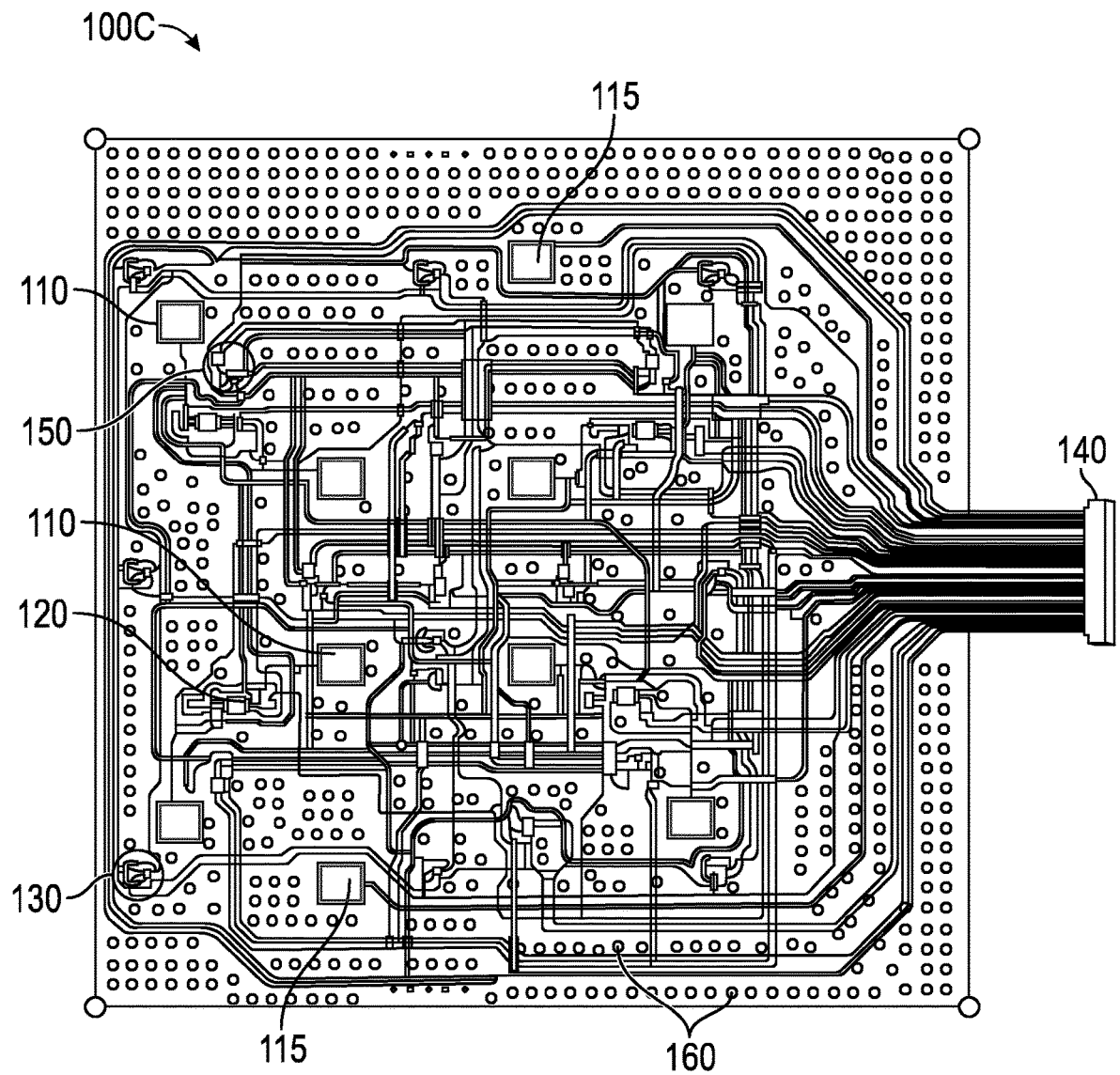
Figure 1D:
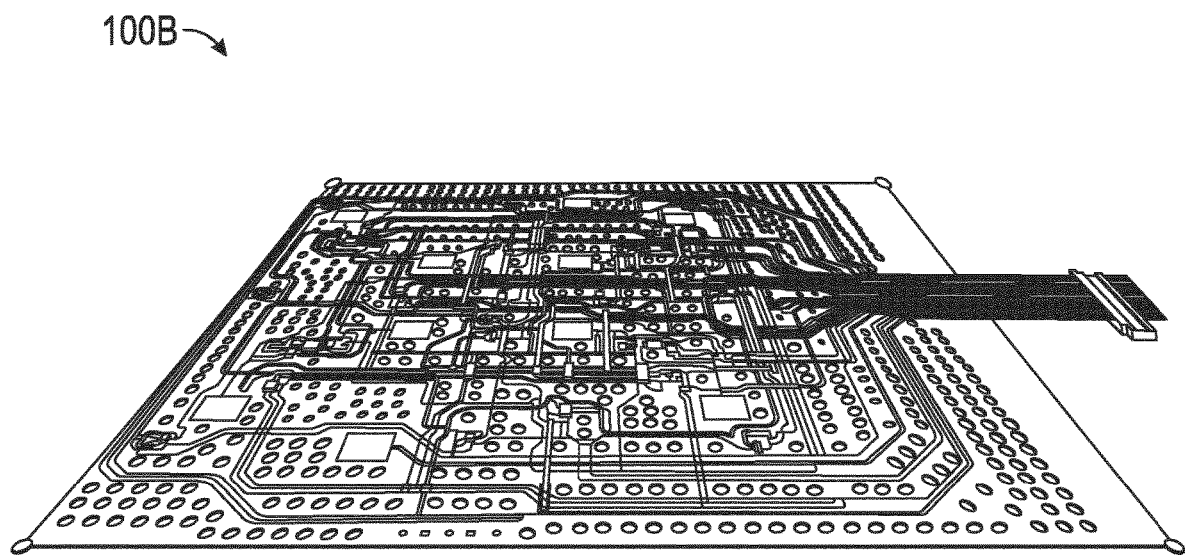

In some implementations, a number of sensor technologies can be used in wound dressings or one or more components forming part of an overall wound dressing apparatus. For example, as illustrated in FIGS. 1B-1D, one or more sensors can be incorporated onto or into a substrate (such substrate can be referred to as "sensor integrated substrate" or "sensor enable substrate"). The substrate is illustrated as having a square shape, but it will be appreciated that the substrate may have other shapes such as rectangular, circular, oval, etc. In some cases, a substrate supporting one or more sensors can be provided as an individual material layer that is placed directly or indirectly over or in a wound. The sensor integrated substrate can be part of a larger wound dressing apparatus. In some cases, the sensor integrated substrate is part of a single unit dressing. Additionally or alternatively, the sensor integrated substrate can be placed directly or indirectly over or in the wound and then covered by a secondary wound dressing, which can include one or more of gauze, foam or other wound packing material, a superabsorbent layer, a drape, a fully integrated dressing like the Pico or Allevyn Life dressing manufactured by Smith & Nephew, or the like.

The sensor integrated substrate can be placed in contact with a wound and can allow fluid to pass through the substrate while causing little to no damage to the tissue in the wound. The substrate can be flexible, elastic, extensible, or stretchable or substantially flexible, elastic, extensible, or stretchable in order to conform to or cover the wound. For example, the substrate can be made from a stretchable or substantially stretchable material, such as one or more of polyurethane, thermoplastic polyurethane (TPU), silicone, polycarbonate, polyethylene, polyimide, polyamide, polyester, polyethelene tetraphthalate (PET), polybutalene tetreaphthalate (PBT), polyethylene naphthalate (PEN), polyetherimide (PEI), along with various fluropolymers (FEP) and copolymers, or another suitable material.

Stretchable or substantially stretchable material can be stretched to 5% or less or more, 10% or less or more, 20% or less or more, or more than 20% of its starting dimensions, such as length or width. In some cases, the stretchable or substantially stretchable material can return to within 5% or less or more of the starting dimensions (such as length or width) after being stretched.

In some cases, the substrate can include one or more flexible circuit boards, which can be formed of flexible polymers, including polyamide, polyimide (PI), polyester, polyethylene naphthalate (PEN), polyetherimide (PEI), along with various fluropolymers (FEP) and copolymers, or the like. One or more sensors can be incorporated into a two-layer flexible circuit. In some scenarios, the one or more circuit boards can be a multi-layer flexible circuit board.

In some cases, the sensor integrated substrate can incorporate adhesive, such as a wound contact layer as described herein, that adheres to wet or dry tissue. In some cases, one or more sensors, which can be positioned one or more flexible circuits, can be incorporated into any layer of the wound dressing. For example, a wound contact layer can have cutouts or slits that allow for one or more sensors to protrude out of the lower surface of the wound contact layer and contact the wound directly. In some situations, one or more sensors can be incorporated into or encapsulated within other components of a wound dressing, such as an absorbent layer.

As shown in FIGS. 1B-1D, a sensor integrated substrate 100B can support a plurality of electronic components and a plurality of electronic connections interconnecting at least some of the components. The electronic components can be one or more of any electronic components described herein, such as a sensor, amplifier, capacitor, resistor, inductor, controller, processor, diode, or the like. The electronic connections can electrically connect one or more of the electronic components. The electronic connections can be can be traces or tracks printed on the substrate, such as using copper, conductive ink (such as silver ink, graphite ink, carbon ink, etc.), or the like. At least some of the electronic connections can be flexible or stretchable or substantially flexible or stretchable.

The plurality of electronic components can include one or more impedance or conductivity sensors 110, which can be arranged in an outer 4×4 grid and an inner 4×4 grid as illustrated in FIGS. 1B-1D. Sensors 110 are illustrated as pads configured to measure impedance or conductivity of tissue across any pair of the pads. Two (or more) excitation pads 115 can be arranged as illustrated to provide the excitation signal across the pads, which is conducted by the tissue and responsive to which impedance or conductance of the tissue can be measured across the pads 110. Electrical components, such as one or more amplifiers 120, can be used to measure impedance or conductance of the tissue. Impedance or conductance measurements can be used to identify living and dead tissue, monitor progress of healing, or the like. The arrangement of the pads 110 in the inner and outer grids can be used to measure the impedance or conductance of the wound, perimeter of the wound, or tissue or areas surrounding the wound.

The plurality of electronic components can include one or more temperature sensors 130 configured to measure temperature of the wound or surrounding tissue. For example, nine temperature sensors arranged around the perimeter of the substrate 100B. One or more temperature sensors can include one or more thermocouples or thermistors. One or more temperature sensors can be calibrated and the data obtained from the one or more sensors can be processed to provide information about the wound environment. In some cases, an ambient sensor measuring ambient air temperature can also be used to assist in eliminating problems associated with environment temperature shifts.

The plurality of electronic components can include one or more optical sensors 150. One or more optical sensors 150 can be configured to measure wound appearance or image the wound. In some cases, a light source or illumination source that emits light and a light sensor or detector that detects light reflected by the wound are used as one or more optical sensors. The light source can be a light emitting diode (LED), such as one or more of white LED, red, green, blue (RGB) LED, ultraviolet (UV) LED, or the like. The light sensor can be one or more of an RGB sensor configured to detect color, infrared (IR) color sensor, UV sensor, or the like. In some cases, both the light source and detector would be pressed up against the skin, such that light would penetrate into the tissue and take on the spectral features of the tissue itself. In some scenarios, one or more optical sensor can include an imaging device, such as a charge-coupled device (CCD), CMOS image sensor, or the like.

In some cases, ultra bright LEDs, an RGB sensor, and polyester optical filters can be used as components of the one or more optical sensors to measure through tissue color differentiation. For example, because surface color can be measured from reflected light, a color can be measured from light which has passed through the tissue first for a given geometry. This can include color sensing from diffuse scattered light, from an LED in contact with the skin, or the like. In some embodiments, an LED can be used with a proximal RGB sensor to detect the light which has diffused through the tissue. The optical sensors can image with diffuse internal light or surface reflected light.

One or more of the plurality of electronic components can be controlled by a control module. The control module can receive and process one or more measurements obtained by the one or more sensors. An external control module, such as 24 illustrated in FIG. 1A, can be connected to at least some of the plurality of electronic components via a connector 140. In some cases, the connector 140 can be positioned at the end of a conductive track portion as illustrated in FIG. 1C or attached to the conductive track portion at a position away from the end as illustrated in FIG. 1B (such as, attached to the top of the track portion with glue). The control module can include one or more controllers or microprocessors, memory, or the like. In some cases, one or more controllers can be positioned on the substrate, and the connector 140 is not used. In some cases, data and commands can be communicated wirelessly, such as by a transceiver positioned on the substrate, and the connector 140 is not used.

In some cases, additional or alternative sensors can be positioned on the substrate, such as one or more pH sensors, pressure sensors, perfusion sensors, or the like.

In some cases, a substrate can be perforated as illustrated in FIGS. 1C-1D. A plurality of perforations 160 can be formed in the substrate 100C, allowing fluid to pass through the substrate. It may be advantageous to use a perforated substrate in conjunction with application of negative pressure wound therapy, during which reduced pressure is applied to the wound covered by a dressing and which causes removal of fluid (such as wound exudate) from the wound. Perforations 160 can be formed around a plurality of electronic components and connections as illustrated in FIGS. 1B-1D. Perforations 160 can be formed as slits or holes. In some cases, perforations 160 can be small enough to help prevent tissue ingrowth while allowing fluid to pass through the substrate.

In some cases, any of the wound dressings or wound dressing components described herein can be part of a kit that also includes a negative pressure wound therapy device. One or more components of the kit, such as the sensor integrated substrate, secondary dressing, or the negative pressure wound therapy device can be sterile.

Any of the embodiments disclosed herein can be used with any of the embodiments described in International Patent Publication No. WO2017/195038, titled "SENSOR ENABLED WOUND MONITORING AND THERAPY APPARATUS," International Patent Publication No. WO2018/189265, titled "COMPONENT STRESS RELIEF FOR SENSOR ENABLED NEGATIVE PRESSURE WOUND THERAPY DRESSINGS," International Patent Application No. PCT/EP2018/069886, titled "SKEWING PADS FOR IMPEDANCE MEASUREMENT," and International Patent Application No. PCT/EP2018/075815, titled "SENSOR POSITIONING AND OPTICAL SENSING FOR SENSOR ENABLED WOUND THERAPY DRESSINGS AND SYSTEMS," each of which is incorporated by reference in its entirety.

Encapsulation and Stress Relief

In some cases, the substrate can be coated to encapsulate or coat one or more of the substrate or components supported by the substrate. Coating can provide biocompatibility, shield or protect the electronics from coming into contact with fluids, provide padding for the electronic components to increase patient comfort, or the like. Such coating cam be sometimes referred to as "conformal coat" or "soft coat." Soft coat can be stretchable or substantially stretchable. Soft coat can be hydrophobic or substantially hydrophobic.

In some cases, while it may be desirable for a substrate to be stretchable or substantially stretchable to better conform to or cover the wound, at least some of the electronic components or connections may not be stretchable or flexible. In such instances, undesirable or excessive localized strain or stress may be exerted on the one or more electronic components, such as on the supporting area or mountings of an electronic component, when the substrate is positioned in or over the wound. For example, such stress can be due to patient movement, changes in the shape or size of the wound (such as, due to its healing), or the like. Such stress may cause movement, dislodgment, or malfunction of the one or more electronic components or connections (for example, creation of an open circuit from a pin or another connector becoming disconnected). Alternatively or additionally, it may be desirable to maintain the position of one or more electronic components, such as one or more sensors, in the same or substantially same location or region with respect to the wound (such as, in contact with the wound) so that measurements collected by the one or more electronic components accurately capture changes over time in the same or substantially same location or region of the wound. While the surface of the stretchable substrate may move when, for example, the patient moves, it may be desirable to maintain same or substantially same locations of one or more electronic components relative to the wound.

To address these problems, in some cases, non-stretchable or substantially non-stretchable coating (such coating can sometimes be referred to as "hard coat") can be applied to one or more electronic components, one or more electronic connections, or the like. Hard coat can provide one or more of reinforcement or stress relief for one or more electronic components, one or more electronic connections, or the like. Hard coating can be formed from acrylated or modified urethane material. For example, hard coat can be one or more of Dymax 1901-M, Dymax 9001-E, Dymax 20351, Dymax 20558, Henkel Loctite 3211, or another suitable material. Hard coat can have viscosity from about 13,500 cP to 50,000 cP before being cured or from about 3,600 cP to about 6,600 cP before being cured. In some cases, hard coat can have viscosity of no more than about 50,000 cP. Hard coat can have hardness from about D40 to about D65 and/or linear shrinkage of about 1.5-2.5%.

In some cases, another coating (or coatings) can be applied to encapsulate or coat one or more of the substrate or components supported by the substrate, such as the electronic connections or the electronic components. Coating can provide biocompatibility, shield or protect the electronics from coming into contact with fluids, provide padding for the electronic components to increase patient comfort, or the like. As used herein, biocompatible can mean being in compliance with one or more applicable standards, such as ISO 10993 or USP Class VI. As described herein, such coating can be sometimes referred to as "conformal coat" or "soft coat."

Soft coat can be formed from one or more suitable polymers, adhesives, such as 1072-M adhesive (for example, Dymax 1072-M), 1165-M adhesive (such as, Dymax 1165-M), parylene (such as, Parylene C), silicones, epoxies, urethanes, acrylated urethanes, acrylated urethane alternatives (such as, Henkel Loctite 3381), or other suitable biocompatible and substantially stretchable materials. Soft coat can be thin coating, for example, from about 80 microns or less up to several millimeters or more. Soft coat can have hardness lower than about A100, A80, A50 or lower. Soft coat can have elongation at break higher than about 100%, 200%, 300% or more. Soft coat can have viscosity of about 8,000-14,500 centipoise (cP). In some cases, coating can have viscosity no less than about 3,000 cP. In some cases, coating can have viscosity less than about 3,000 cP.

Any of the hard or soft coats described herein can be applied by one or more of laminating, adhering, welding (for instance, ultrasonic welding), curing by one or more of light, UV, thermal (such as, heat), or the like. Any of the hard or soft coat described herein can be transparent or substantially transparent to facilitate optical sensing. Any of the coatings described herein can retain bond strength when subjected to sterilization, such as EtO sterilization. Any of the coatings described herein can be modified to fluoresce, such as under UV light.

Figure 2A:
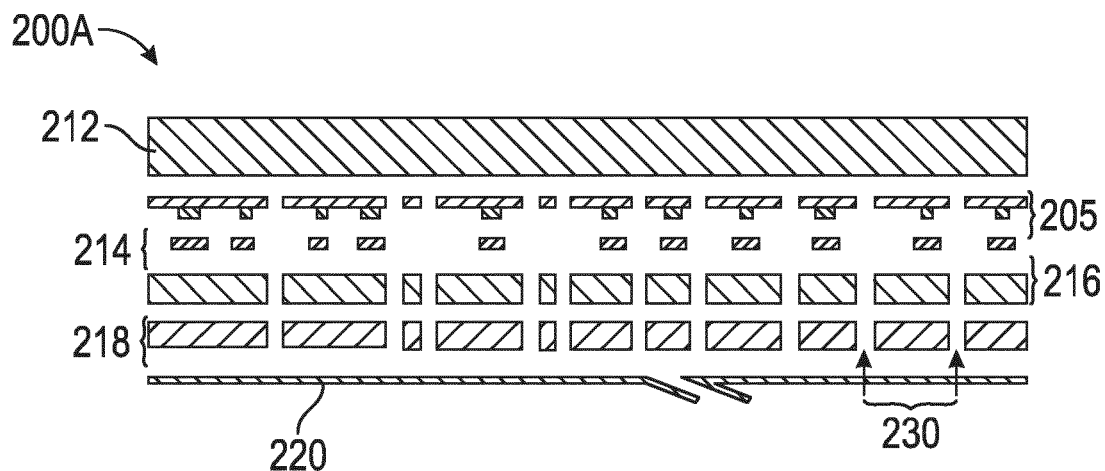
FIGS. 2A-2B illustrates cross-sections of wound dressings.
Figure 2B:
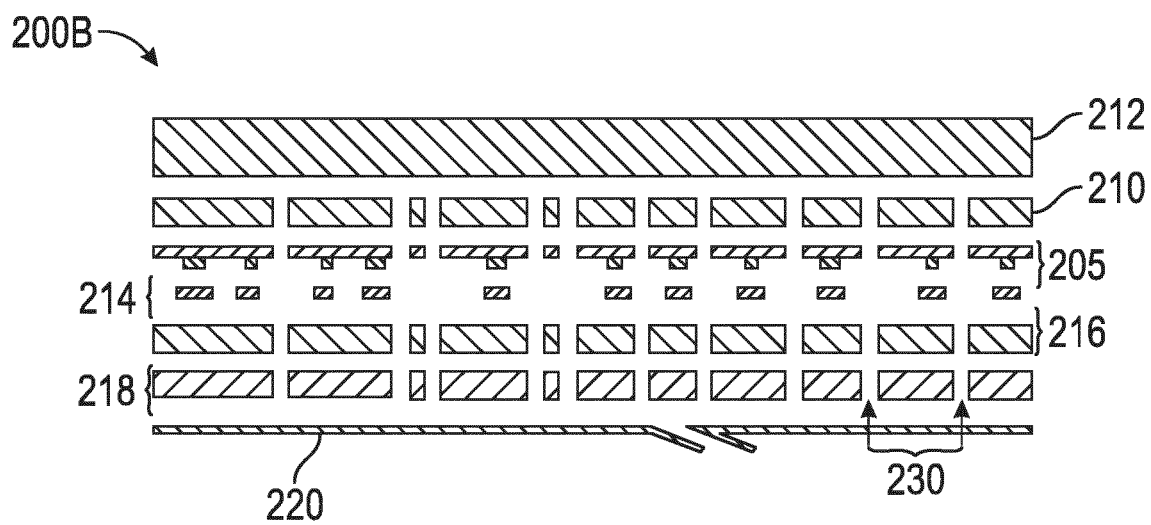

FIGS. 2A-2B illustrate cross-sections of wound dressings that include sensor integrated substrates. Dressing 200A shown in FIG. 2A can include a sensor integrated substrate 205 supporting a plurality of electronic components (shown as protruding from the substrate) and a plurality of electronic connections, as described herein. The dressing 200A can include hard coat 214, applied to one or more electronic components or connections. In some cases, hard coat can be applied to areas where electronic components are connected to electronic connections. This can reinforce these connections. In some cases, hard coat can be applied to each of the one or more of the electronic components or connections.

The dressing 200A can include soft coat 216, which can be applied to the entire wound facing side of the substrate. Soft coat 216 can be applied to an entire or substantially entire area of the wound facing side of the substrate to encapsulate the substrate, electronic components, and connections. In some cases, soft coat 216 can be applied to certain regions of the substrate, such as those regions supporting one or more of electronic components or connections.

The dressing 200A can include a wound contact layer 218. The wound contact layer 218 can include adhesive material configured to adhere the substrate to the wound, which can facilitate maintaining contact of one or more sensors with the wound. The wound contact layer 218 can be formed from silicone. The silicone material can be low tac (or tack) silicone. The wound contact layer 218 can include silicone adhesive mounted on a film. In some cases, the wound contact layer 218 can be similar to the material used in Allevyn Life Non-Bordered dressing manufactured by Smith & Nephew.

The wound contact layer 218 can be applied to entire or substantially entire area of the wound facing side of the substrate. In some cases, the wound contact layer 218 can be applied to certain regions of the substrate, such as those regions supporting one or more of electronic components or connections.

As illustrated in FIG. 2A, a plurality of perforations 230 can be formed through one or more of the substrate, hard coat, soft coat, and wound contact layer. As described herein, perforations can be made in regions or areas of the substrate that do not support electronic components or connections.

The dressing 200A can include a protective layer 220 applied to the wound contact layer 218. The protective layer 220 can be made of paper, such as laminated paper. The protective layer 220 can protect the wound contact layer 218 prior to use and facilitate easy application for a user. The protective layer 218 can include a plurality (such as two) handles. The handles can be applied in a folded configuration, in which a slit separating the handles is covered by one of handles folded over the slit. In some cases, the protective layer 218 can be similar to the protective layer used in the Allevyn Life Non-Bordered dressing.

As illustrated, a wicking layer 212 can be positioned over an opposite, non-wound facing side of the substrate. The wicking layer 212 can facilitate passage of fluid through the layers below the wicking layer. For example, the wicking layer can transport (or "wick") fluid away from the lower layers, such as from the substrate, toward one or more upper layers positioned over the wicking layer 212. Such one or more upper layers can include one or more absorbent materials as described herein. In some cases, the wicking layer 212 is formed from foam, such as foam similar to that used in the Allevyn Life Non-Bordered dressing. The wicking layer can be extensible or substantially extensible.

As illustrated in the dressing 200B of FIG. 2B, additional layer of soft coat 210 can be positioned over the non-wound facing side of the substrate between the substrate and the wicking layer 212. For example, soft coat 210 can protect the non-wound facing side of the substrate from fluid if the substrate is formed from material that is not impermeable to fluid. In such case, soft coat 210 can be hydrophobic or substantially hydrophobic. Soft coat 210 can be made of same or different material than soft coat 218. Soft coat 210 can be perforated as illustrated and described. In some cases, soft coat can encapsulate the entire substrate, including both the wound facing and non-wound facing sides.

Figure 3A:
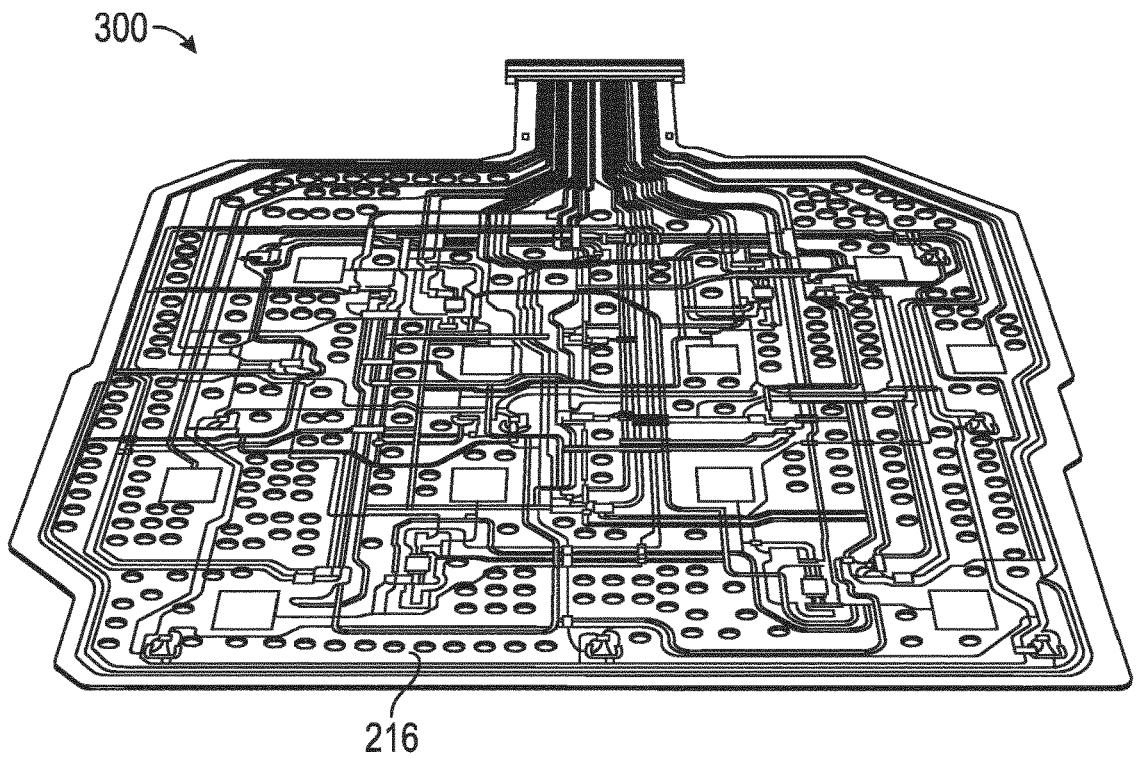
FIGS. 3A-3B illustrate perspective and top views of a perforated substrate supporting electronic components.
Figure 3B:
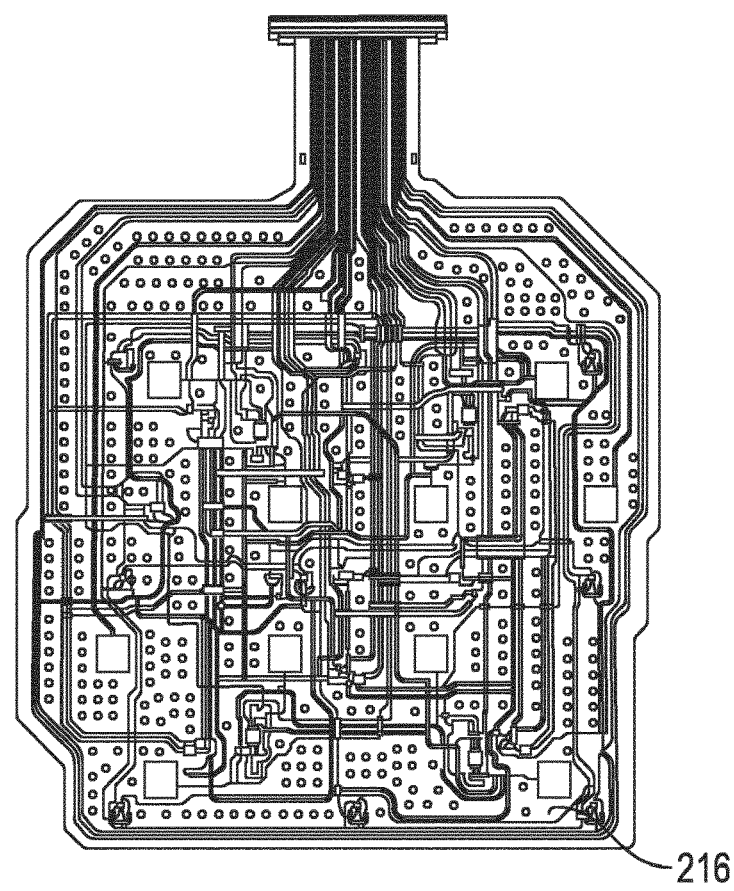

FIGS. 3A-3B illustrate coated sensor integrated substrates 300. The substrates 300 are illustrated with non-wound facing side 216 up. The substrates 300 can be similar to any of the substrates described herein.

Any of the embodiments disclosed herein can be used with any of the embodiments described in International Patent Application No. PCT/EP2018/069883, titled "BIOCOMPATIBLE ENCAPSULATION AND COMPONENT STRESS RELIEF FOR SENSOR ENABLED NEGATIVE PRESSURE WOUND THERAPY DRESSINGS," which is incorporated by reference in its entirety.

In some implementations, borders or edges of the substrate can be smoothed by cuts, have smooth contours, include fibers, or the like to improve patient comfort.

In some cases, the substrate can include one or more antennas for wireless communication. For example, one or more antennas can be printed as one or more connections or traces on the substrate. The one or more antennas can be used to communicate measurement data collected by the one or more sensors without using a controller, such as the controller 24. The one or more antennas can additionally be used to receive power wirelessly from a power source. In certain cases, the one or more antenna traces can be positioned on a substantially non-stretchable material (as described herein) such that the resonant frequencies of the one or more antennas remain fixed when the substrate is placed under stress when in use on a patient. Fixing the one or more resonant frequencies can be advantageous for certain communication protocols, such as RFID.

Design Rules for Positioning Components on Perforated Substrate

In some cases, a plurality of perforations can be formed in a substrate as depicted in FIGS. 1C-1D. The positioning of perforations, such as one or more of the size, number, density, or distance between adjacent perforations, can be dictated by a particular application in which the substrate will be used, such as negative pressure wound therapy. For example, it may be desirable to form perforations of a particular minimum size and at a particular maximum distance from adjacent one or more perforations in order to ensure that fluid moves through the substrate without undesirable pooling at a region of the wound below the substrate (which can cause maceration of skin, infection, or the like). On the other hand, because it may be undesirable to form perforations through the electrical components and connections, positioning of the perforations can provide a set of limitations or constraints on the dimensions and positioning on the substrate of the electrical components and connections to ensure that the electronics positioned on the substrate functions correctly and efficiently. Such set of constraints can sometimes be referred to as "design rules." In some cases, additional or alternative set of limitations or constraints can be dictated by one or more requirements of maintaining electrical signal integrity along the traces. The following paragraphs describe at least some of the design rules.

Figure 4:
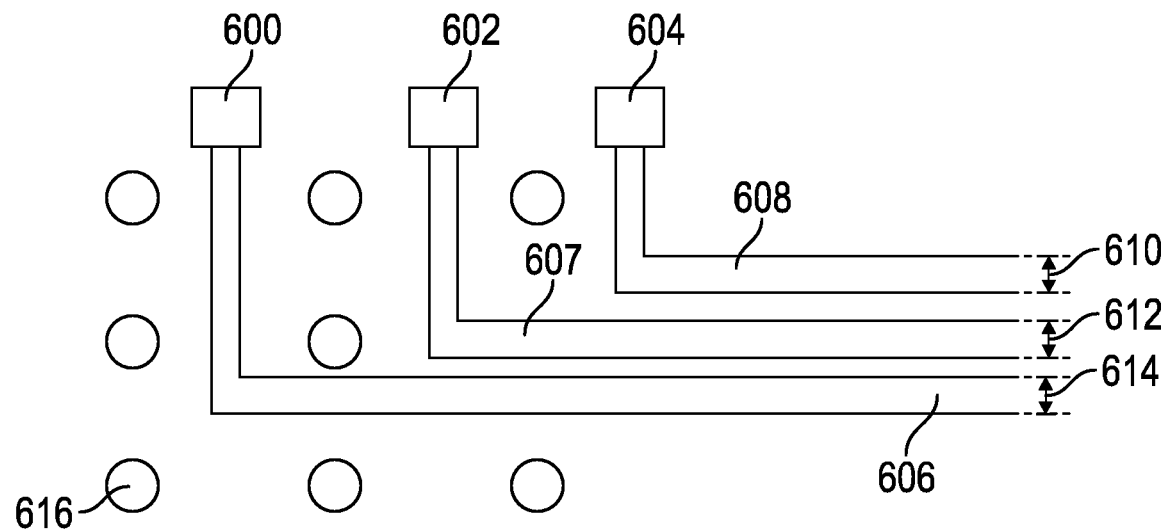
FIG. 4 illustrates components and traces positioned on a perforated substrate.

FIG. 4 illustrates a plurality of electronic components and traces positioned on a substrate with a plurality of perforations 616. Any of the perforations 616 can be circular or triangle, square, cross-shaped, star-shape, or the like. In some cases, any of the perforations 616 can have an opening of about 0.400 mm to about 2.00 mm, such as an opening with a diameter of 1.8 mm (or less or more). The components positioned on the substrate can include a temperature sensor 600, an optical sensor 602, and a conductivity sensor or pad 604. The components can be connected to other parts of the circuitry by traces 606, 607, and 608. The traces can be made out of conductive ink (as described herein) or another conductive material that is suitable for being positioned on the substantially flexible substrate as described herein. The traces can be positioned onto the substrate by screen printing. In some cases, the traces can have a thickness of less than about 10 μm, about 10 μm, or more than about 10 μm. The traces can be positioned onto the substrate by two screen printings. In such cases, the traces can have a thickness of less than about 20 μm, about 20 μm, or more than about 20 μm. In some instances, thicker traces can advantageously have smaller variability in impedance (and/or smaller overall impedance) than thinner traces, which can improve signal integrity of an electrical signals conducted by the traces.

Figure 5:
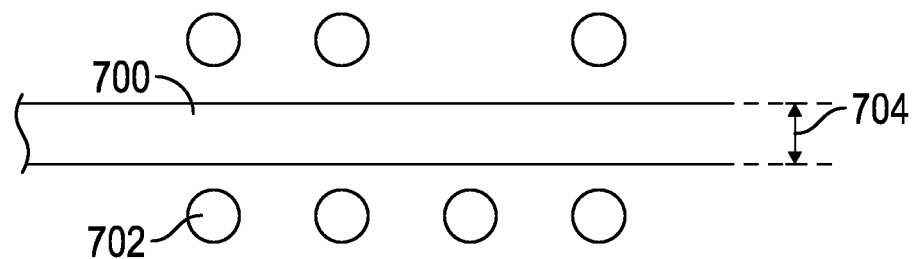
FIG. 5 illustrates a trace positioned on a perforated substrate.

As shown in FIG. 4, the traces 606, 607, and 608 can be positioned to maneuver around the perforations 616. Although three components 600, 602, and 604 and three traces 606, 607, and 608 are illustrated, in some cases, there can be more or less components and/or traces. In order to reduce variability in impedance, the traces can have minimum width requirements. Each of the traces 606, 607, and 608 can have its own minimum width requirement or one or more of the traces can share same minimum width requirement. Positioning of the perforations, such as the size of perforations and distance between adjacent perforations, can constrain the minimum width of the traces, as illustrated in FIG. 5. Because positioning of the perforations may not allow the minimum width of the traces to exceed certain dimension(s), one or more properties of the traces, such as type of material(s) used to make the traces, may need to be selected accordingly. In some cases, traces that are configured to conduct digital signals can have smaller minimum width requirements that traces that are configured to conduct analog signals (for example, because impedance variability for a trace conducting analog signals may need to be smaller since analog signals are more susceptible to signal degradation than digital signals). In some cases, the minimum width of a digital signal trace (such as, temperature or optical signal trace) can be about 0.3 mm (or less or more), and the minimum width of analog signal traces (such as, conductivity signal trace) can be about 0.5 mm (or less or more), about 1.0 mm (or less or more), or the like. Minimum widths of the traces 606, 607, and 608 are illustrated as 614, 612, and 610 respectively. In some implementations, if conductive ink with lower impedance is used as the material for at least some of the traces, the width of such traces can be decreased. This may be due to smaller variability in impedance along a trace formed of conductive ink with lower impedance than that of trace formed of conductive ink with higher impedance.

In some cases, one or more of power or ground traces can also have minimum width requirements. For example, a power source trace (such as, 15V to power analog electronics) can have a minimum width of about 1.0 mm (or less or more). As another example, a power source trace for a lower voltage signal (such as, 3V to power digital electronics) can have a minimum width of about 0.5 mm (or less or more). In some cases, one or more of power or ground traces for digital circuitry, such as a control signal for a light sensor of an optical sensor, can have a wider minimum width requirement than those of digital signal traces. This can be due to the power and/or ground traces needing to accommodate the switching noise associated with operation of digital circuitry. For instance, a power trace for a light sensor can have a minimum width of about 0.75 mm (or less or more).

In some instances, analog and digital grounds can be formed as separate one or more traces with different minimum width. As described herein, the analog traces can have wider width requirements because analog traces have less tolerance for increased or higher variability impedance.

In some cases, one or more of the electronic components or traces are positioned a minimum distance away from the perforations, such as from the edge or center of one or more adjacent perforations. This can advantageously improve electrical immunity of the substrate and/or circuitry supported by the substrate by, for example, reducing the risk of electrical current or electrostatic discharge being conducted from an electronic component or electrical trace to the tissue through a perforation, particularly in operation when conductive fluid, such as exudate, fills the perforation.

FIG. 5 illustrates a trace 700 positioned on a substrate with perforations 702. As shown in FIG. 5, the width of the trace is constrained or limited by the positioning of the perforations 702, such as by the distance or spacing between adjacent perforations. Due to such limitations, the minimum width of the trace 700 can be no more than the illustrated width 704.

Figure 6:
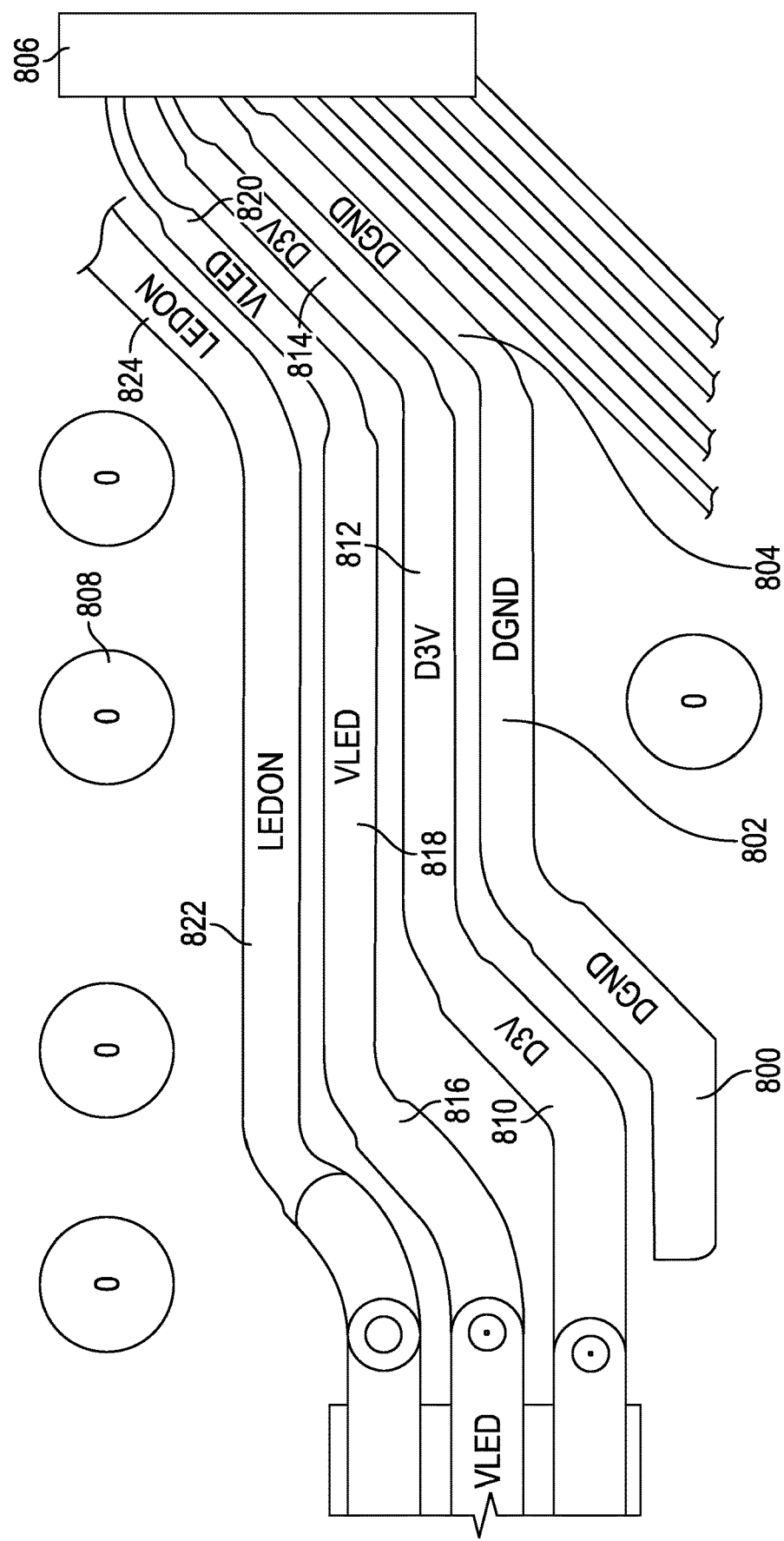
FIG. 6 illustrates a plurality of traces positioned on a perforated substrate.

In some cases, traces of same or different widths can be connected to one another (or a trace can have portions having different width connected to one another). In order to improve signal integrity, it can be advantageous to make such connections or transitions be one or more of gradual or smooth. Such transitions can sometimes be referred to as "teardrops." For example, the connections or transitions can be without sharp corners or edges (such as 90 degree corners). This can reduce variability in impedance and improve signal integrity. FIG. 6 illustrates a plurality of traces connecting to a connector 806 (which can be similar to the connector 140 illustrated in FIGS. 1B-1D. The plurality of traces are positioned on a substrate with perforations 808. As shown in FIG. 6, trace 822 can carry a light source (such as, LED) on/off signal. Such signal can be a digital signal. Trace 822 can taper into a narrower portion of the trace 824 as it approaches the connector 806. As illustrated, the transition between portions 822 and 824 can be gradual and smooth. For example, the transition can be elongated and round. Trace 816 can carry a voltage signal for the light source. Trace 816 can taper into narrower portions of the trace 818 and 820 as the trace approaches the connector 806. The transitions from portions 816 to 818 and 818 to 820 can be gradual and smooth, such as elongated and round, as illustrated in FIG. 6.

Trace 810 can carry a digital power source signal, such as a 3V signal. Trace 810 can taper into narrower portions of the trace (or other traces) 812 and 814 as the trace approaches the connector 806. The transitions from portions (or traces) 810 to 812 and 812 to 814 cam be gradual and smooth, such as elongated and round, as illustrated in FIG. 6. Trace 800 can carry a digital ground signal. Trace 800 can taper into narrower portions of the trace (or other traces) 802 and 804 as the trace approaches the controller 806. The transitions from portions (or traces) 800 to 802 and 802 to 804 cam be gradual and smooth, such as elongated and round, as illustrated in FIG. 6.

In some cases, the width of the traces narrows (or tapers) closer to the connector 806 because of space constraints caused by connecting numerous traces to the connector 806. In some instances, any of the traces can include more than two gradual and smooth portions.

In some cases, unlike with a printed circuit board (PCB) substrate, it may not be possible to provide multiple layers for increasing the area in which the traces can be routed on substantially flexible substrates described herein. With such substrates, traces may need to be printed on a single side of the substrate, such as on the wound facing side or the non-wound facing side. To increase the area for routing the traces on such substrates, two layers can be formed by routing the traces left/right or horizontally (referred to as the first layer, which can serve as a bottom layer using PCB terminology) and up/down or vertically (referred to as the second layer, which can serve as a top layer using PCB terminology). Additional layers can be formed in some cases by routing the traces, for example, diagonally. Different layers can be separated by a mask made out of non-conductive material, such as nonconductive paint. For example, as described herein, a mask region can be positioned where two traces from first and second layers crossover (unless it is desired for the two traces to be electrically connected).

In some implementations, there can be minimum distance (or gap) requirements between adjacent traces in order to avoid or minimize the risk of creating a short circuit between the adjacent traces (such as, when printing the conductive ink to form the traces). Such minimum distance requirements can be the same or different for traces in the first and second layers. Minimum distance requirements can be constrained by the positioning of the perforations, such as by the distance or spacing between adjacent perforations.

Figure 7:
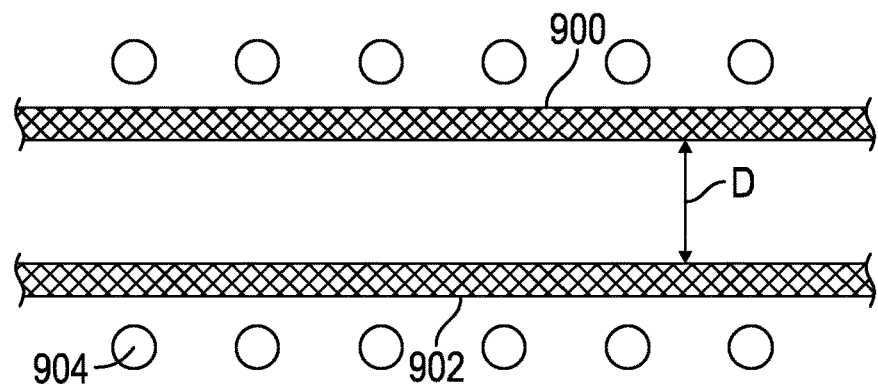
FIG. 7 illustrates adjacent traces separated by a minimum distance.

FIG. 7 illustrates a pair of adjacent traces positioned on a substrate with perforations 904. As shown in FIG. 7, trace 900 and trace 902 are separated by a minimum distance D. Also as shown in FIG. 7, the traces 900 and 902 are positioned in areas of the substrate where there are no perforations 904. In some cases, traces in the first layer (or second layer) can have a minimum distance requirement of at least about 0.2 mm (or more or less). In some cases, traces in the second layer (or first layer) can have a minimum distance requirement of at least about 0.4 mm (or more or less). These differences in the minimum distances may be due to the traces in the first layer (or second layer) being printed before the traces in the second layer (or first layer) are printed.

In some instances, some or all portions of the traces are not parallel. In such instances, the minimum distance D can be measured at the point where the two traces 900, 902 are nearest to each other.

Figure 8:
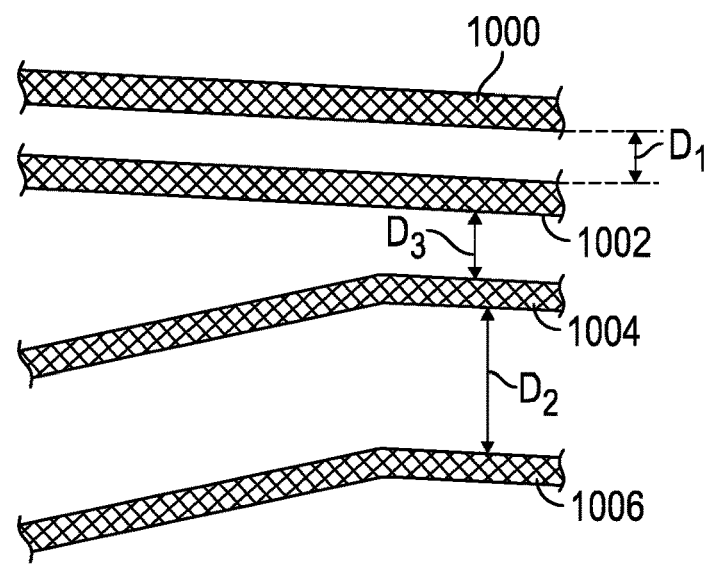
FIG. 8 illustrates two pairs of traces separated by minimum distances.

FIG. 8 illustrates two pairs of traces. As shown in FIG. 8, traces 1000 and 1002, which are oriented in the same direction, are separated by a minimum distance D1. Traces 1004 and 1006 are separated by a minimum distance D2. As shown in FIG. 8, portions of the traces 1004 and 1006 are oriented in a different direction from the traces 1000 and 1002. The two pairs of traces 1000, 1002 and 1004, 1006 are positioned so that there is a minimum distance D3 between the two pairs of traces. Distance D3 can be measured between traces 1002, 1004, which are the two traces from the pairs closest to each other. The two traces from the pairs that are closest to each other can be oriented in different directions. Minimum distances D1, D2, and D3 can be different from one another. In some cases, any two or more minimum distances can be the same.

Figure 9:
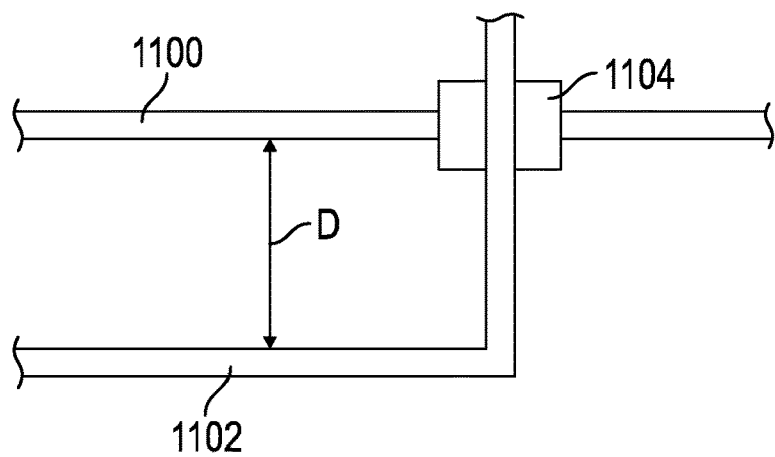
FIG. 9 illustrates two traces positioned in different layers.

As shown in FIG. 9, trace 1100 can be positioned in a horizontal layer and trace 1102 can be positioned at least partially in a vertical layer. As described herein, portions of the traces 1100 and 1102 positioned in the same layer can be separated by a minimum distance D. In some cases, the minimum distance D can be at least about 0.3 mm (or less or more). A mask 1104 can separate the traces 1100 and 1102 in a crossover region where a portion of the trace 1102 positioned in the vertical layer intersects the trace 1100, which is positioned in the horizontal layer. The mask 1104 can be positioned between the traces 1100 and 1102. The mask 1104 can be electrically isolating and can prevent traces 1100, 1102 from being electrically connected to one another. In some embodiments, the mask can be made of nonconductive paint. In some embodiments, the mask can have an area larger than the area of the intersection of the traces.

Figure 10:
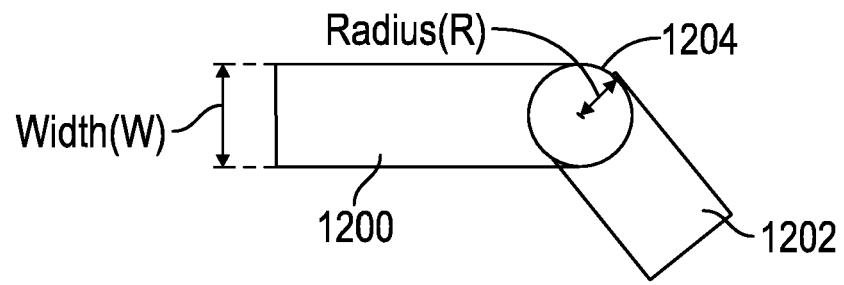
FIG. 10 illustrates two traces joined at a joint.
Figure 11:
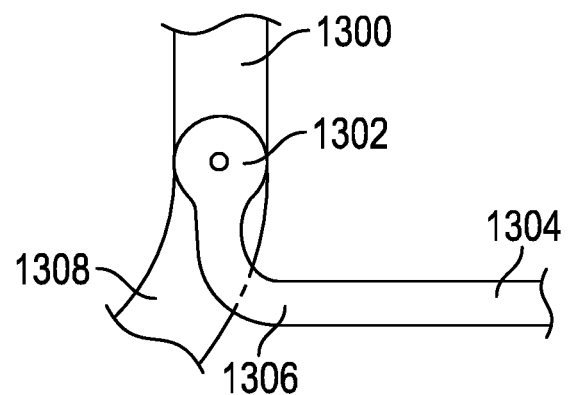
FIG. 11 illustrates one trace meeting another trace at a joint.

FIG. 10 illustrates portions of two traces 1200 and 1202 electrically connected at a connection or joint 1204. The joint 1204 can be designed to minimize or eliminate any changes or increases in the impedance, which can improve signal integrity. The joint 1204 can form an overlap between the two traces. In some cases, as shown in FIG. 10, the joint 1204 can have a circular or substantially circular shape with a radius equal to, for example, at least half of the width of the traces 1200 and 1202 (when the traces have the same or substantially same width W). In some cases, as illustrated in FIG. 11, the radius can be, for example, at least half of the width of a trace having the larger width (when the traces do not have the same width). Sizing the joint 1204 this way can advantageously increase the overlap between the traces. In some instances, the radius of the joint can be more or less than half the width.

In some cases, a joint can be formed as an island on the substrate and the traces can be positioned to touch the island. The island can have round or substantially round shape because such shape can be more advantageous for maintaining signal integrity than, for example, a shape with sharp transitions (such as, rectangular shape with 90 degree transitions).

In some cases, the joint 1204 can have an elongated shape with substantially circular ends. In some embodiments, the elongation can be with respect to the direction of at least one of the traces. The joint 1204 can be made of conductive material. For example, the joint can be made of same or different conductive ink than that of the traces. In some embodiments, the joint can be positioned onto the substrate by first printing a non-circular area and then removing the material (such as, when it dries) to form a circular area.

From the perspective of signal integrity, it can be advantageous to form electrical connections between traces by shaping the traces to avoid formation of any sharp angles or corners (such as 90 degree corners) at or proximal to a joint connecting the traces. As described herein, teardrops can be used for forming at least some electrical connections. This can reduce variability in impedance, reduce parasitic capacitance, or the like, which can lead to improved signal integrity. For example, as shown in FIG. 10, the traces 1200 and 1200 are routed to connect at an angle that is smaller (or more acute) than 90 degrees.

As another example, as described herein, traces of different widths can be connected to one another (or portions of the same trace having different widths can be connected to one another). The traces (or trace portions) can be shaped to have gradual or smooth transitions, such as round transitions, at and/or proximal to a joint connecting the traces (or trace portions).

FIG. 11 illustrates portions of two traces electrically connected at a joint 1302. As shown in FIG. 11, the traces 1300 and 1304 have different widths. Transitioning portions 1306 and 1308 of the traces 1300 and 1304, respectively, proximal to the joint 1302 can be designed to have smooth shapes. The transitioning portions can have substantially round or circular shapes. As shown in FIG. 11, the transitioning portions 1306, 1308 approach the joint 1302 at an angle and have rounded or circular shape (or are arc-shaped). In some instances, the transitioning portions 1306, 1308 can be straight when the respective traces are co-linear or substantially co-linear. In some implementations, a mask isolating a pair of traces in a crossover region can have a smooth shape, such as a substantially round shape.

Figure 12:
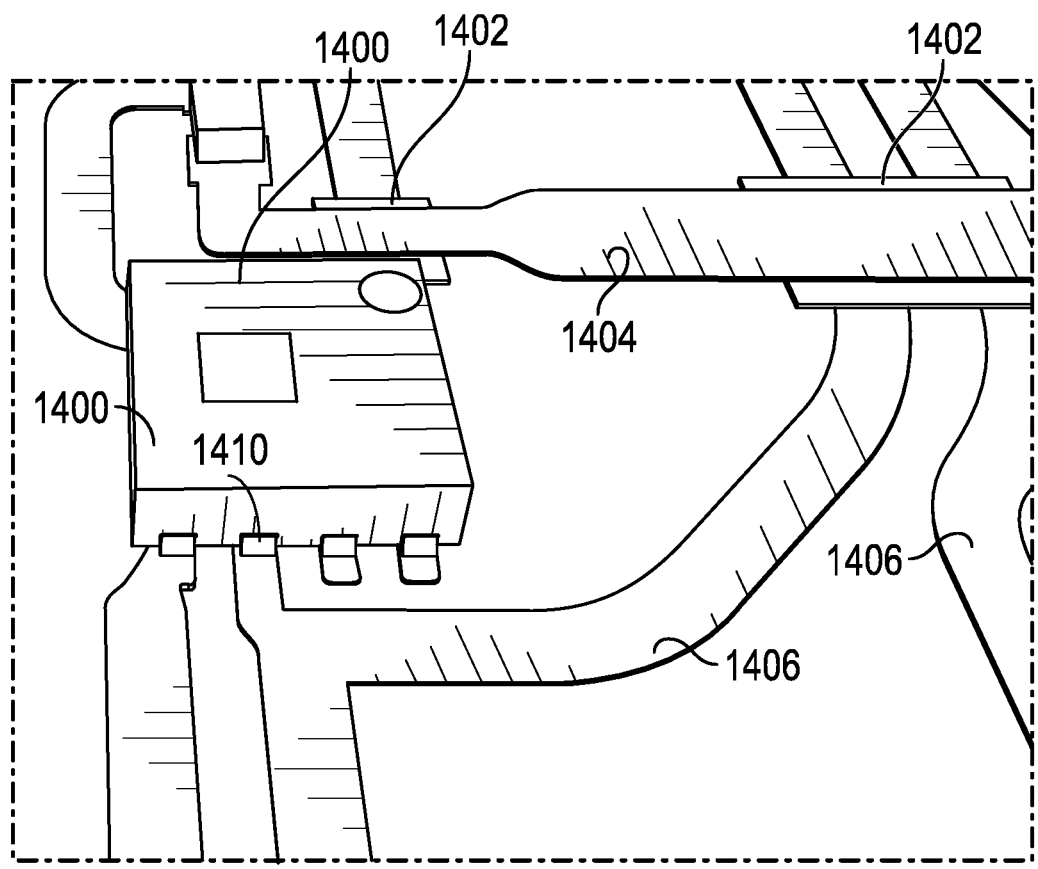
FIG. 12 illustrates a plurality of traces connecting to components.

FIG. 12 illustrates a perspective view of a substrate supporting an electronic component 1400 and traces 1404, 1406. Trace 1406 can be connected to the pins of an electronic component 1400. As described herein, one or more of the traces 1406 can be positioned in a vertical layer, and the trace 1404 can be positioned in a horizontal layer. In some embodiments, the manufacturing method of placing the electronics on the substrate can include of printing more than two layers of traces. The traces 1404 and 1406 can be separated by a mask region 1402 at a point where the traces crossover. The mask region 1402 can be made of a nonconductive material, such as non-conductive paint. In some embodiments, the mask can have an area larger than the area of the intersection of the traces.

Preventing Migration of Traces

As described herein, traces (or tracks) can be made from conductive ink or glue, such as silver ink. It may be possible for conductive material of the traces to migrate or disperse and, in some cases, cause short circuiting between adjacent traces. Migration may have negative impact on signal integrity (particularly for analog signals) and negatively impact patient safety. Migration may be due to coating the substrate, for example, with soft coat as described herein.

Figure 13:
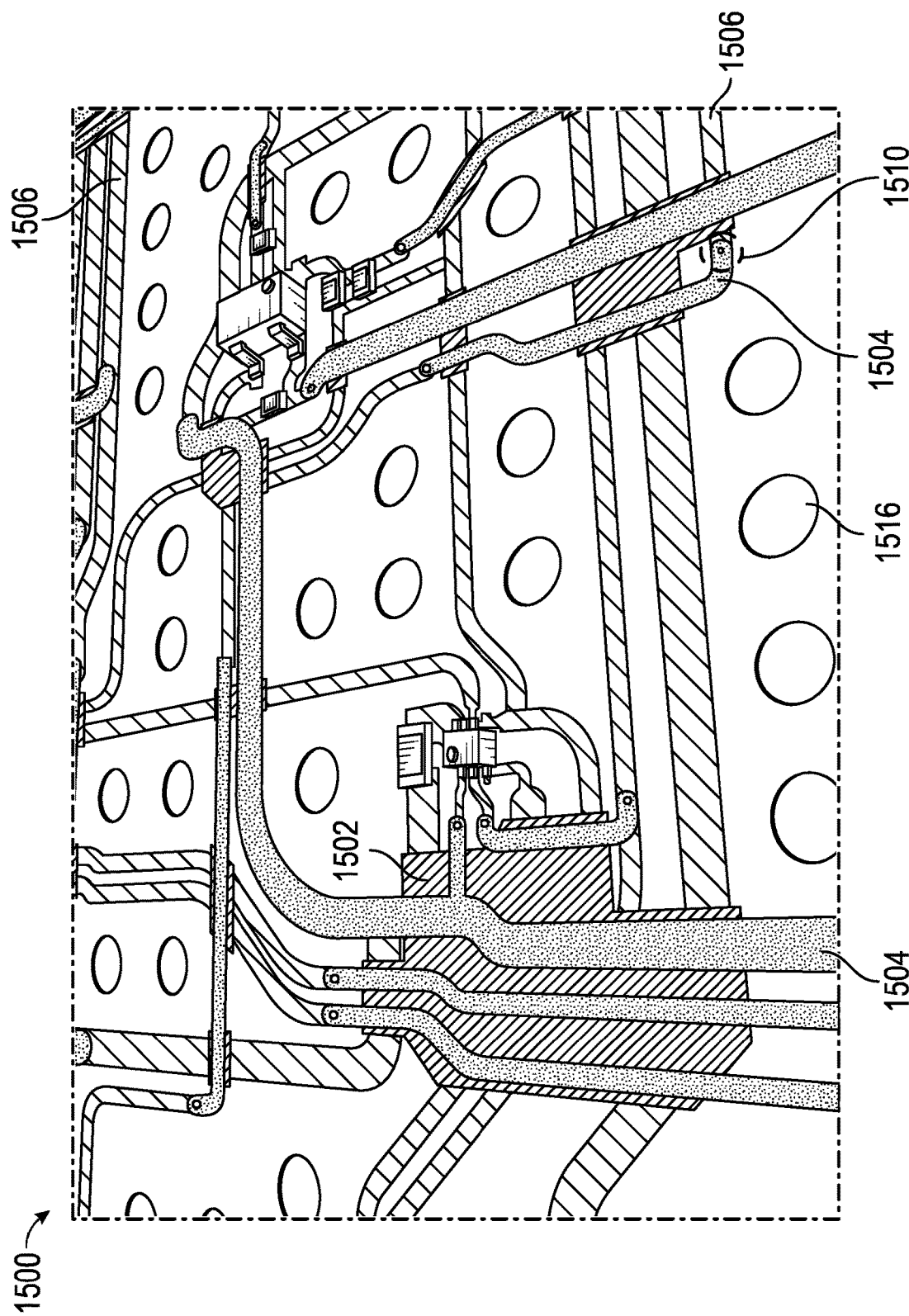
FIG. 13 illustrates traces positioned on a perforated substrate.

Migration can be prevented or reduced by applying one or more masks. FIG. 13 illustrates a substrate 1500, which can be similar to any of the substrates described herein. The substrate 1500 can be perforated with one or more perforations 1516, as described herein (for example, with reference to FIGS. 4-5). The substrate 1500 can include one or more traces 1504 in a vertical layer and one or more traces 1506 in a horizontal layer, as described herein (for example, in connection with FIG. 12). To prevent migration, the traces can be applied on the substrate (such as, printed on the substrate) as follows. Traces in one of the layers (such as, traces 1506 in the horizontal layer or traces 1504 in the vertical layer) can be applied first. After the traces in one of the layers have been applied on the substrate 1500, a first mask can be applied to the substrate 1500. The first mask can protect and isolate the applied traces of one of the layers. For instance, with reference to FIG. 13, a portion of such mask is illustrated as 1502. The first mask can be applied to the entire substrate 1500 with the exception of regions where electrical connection with a trace should be formed, such as a pad (for example, to connect with a pin 1410 of the component 1400 in FIG. 12), region (sometimes referred to as via) connecting the trace to another trace (for example, 1510 in FIG. 13), or the like. After the first mask has been applied, traces in the other layer can be applied to the substrate 1500. Subsequently, a second mask can be applied to the substrate 1500. The second mask can protect and isolate the applied traces. As described herein, the second mask can be applied to the entire substrate 1500 with the exception of regions where electrical connection with a trace should be formed. Application of one or more masks can prevent or minimize migration of the conductive material of the traces.

Multilayer Flexible Substrate

Figure 14A:
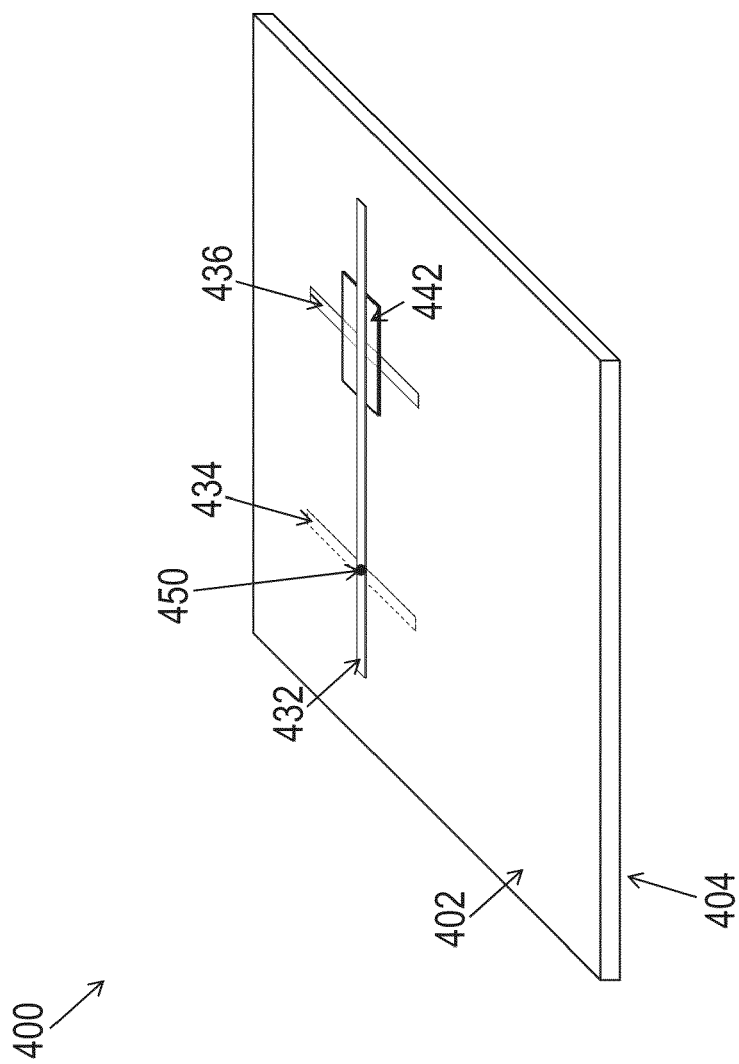
FIGS. 14A-14C illustrate perspective and cross-sectional views of a substrate supporting one or more electronic connections or electronic components.

FIG. 14A illustrates a perspective view of a substrate 400 supporting one or more electronic connections or electronic components. The substrate 400 can be similar to any of the flexible or substantially flexible substrates described herein, such as any of the substrates 100A, 100B, 200, or 300. The substrate 400 can include a first side 402 and second side 404 opposite the first side. The first side 402 can be the wound facing side and the second side 404 can be the non-wound facing side (or vice versa). As described herein, at least one conductive track 432 can be positioned on the first side 402 of the substrate 400. It may be advantageous to position at least another conductive track on the second side 404 of the substrate 400. This can increase the area in which tracks can be routed on the substrate 400, the area for positioning one or more electronic components, and positioning of one or more planes (such as, a ground plane, power plane, etc.). Using printed circuit board (PCB) terminology, the first and second sides 402 and 404 can serve as first and second layers (or top and bottom layers) on which tracks can be routed. This way, two layers can be formed on the substrate.

In some cases, one or more of tracks or components positioned on opposite sides of the substrate 400 may be electrically connected. For example, an antenna can be positioned on a first side of the substrate 400, while at least some of radio frequency (RF) circuitry, which can be configured to transmit and/or receive signals (for example, function as a transceiver), can be positioned on the second side of the substrate 400 (or vice versa). The RF circuitry may be connected to the antenna. As another example, a ground or power plane can at least partially be positioned on a first side of the substrate 400, while one or more electronic components can be positioned on the second side of the substrate 400 (or vice versa). At least some of the one or more electronic components may be connected to the ground or power plane.

Multilayer PCBs may use a via for connecting tracks positioned in different layers of the PCB. A via can include a barrel (for example, a conductive tube filling a drilled hole in the PCB), a pad (for example, connection of each end of the barrel to a component or track), and antipad (for example, a clearance hole between the barrel and a component or track to which the barrel is not connected). Because, unlike a PCB, the substrate 400 can be flexible or substantially flexible, it may not support such vias. In some cases, a conductive connection can be made through the substrate in order to connect one or more tracks or components positioned on the opposite sides of the substrate 400. Connection can be made by passing conductive material through the substrate 400. For example, a perforation can be made the substrate 400 and conductive material can be positioned in the perforation, such as fill the perforation. In some cases, the conductive material can be conductive ink, conductive glue, solder paste, wire, or the like.

Figure 14B:
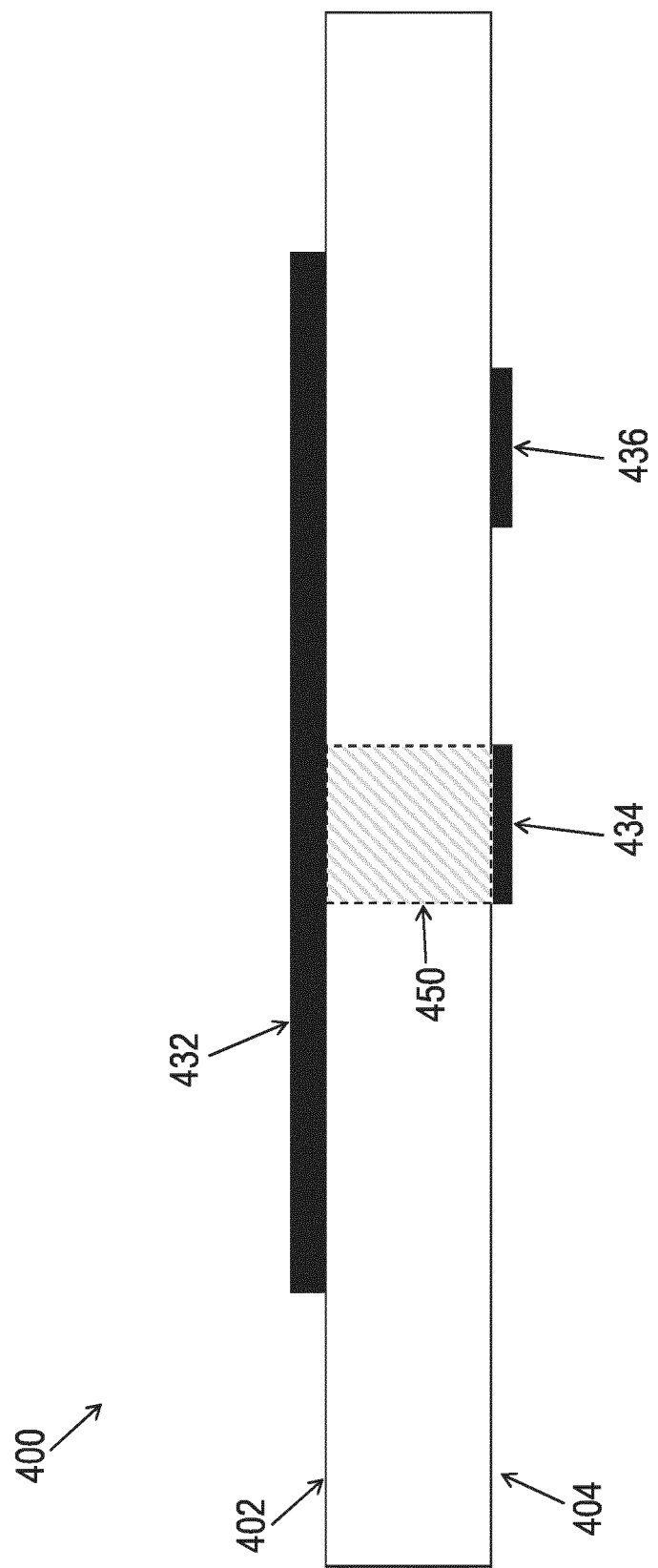

With reference to FIGS. 14A-14B, conductive track 432 positioned on the first side 402 of the substrate 400 can be electrically connected to another conductive track 434 positioned on the second side 404 of the substrate 400 via a connection 450. A portion of track 432 can overlap a portion of track 434. Connection 450 can be formed where the portions of the tracks 432 and 434 overlap. As illustrated in FIG. 14B, which shows cross-sectional view of the substrate 400, connection 450 can be a perforation through the substrate. Conductive material can be positioned in the perforation, such as fill the perforation. Tracks 432 and 434 can cover at least part of the perforation. For example, overlapping portions of the tracks 432 and 434 can cover at least part of the perforation.

As illustrated in FIGS. 14A-14B, track 432 may not be electrically connected to another track 436. With reference to FIG. 14B, track 436 can be positioned on the second side 404 of the substrate 400. Tracks 432 and 436 may not be electrically connected because no connection between the tracks 432 and 436 is formed through the substrate, as shown in FIG. 14B.

Figure 14C:
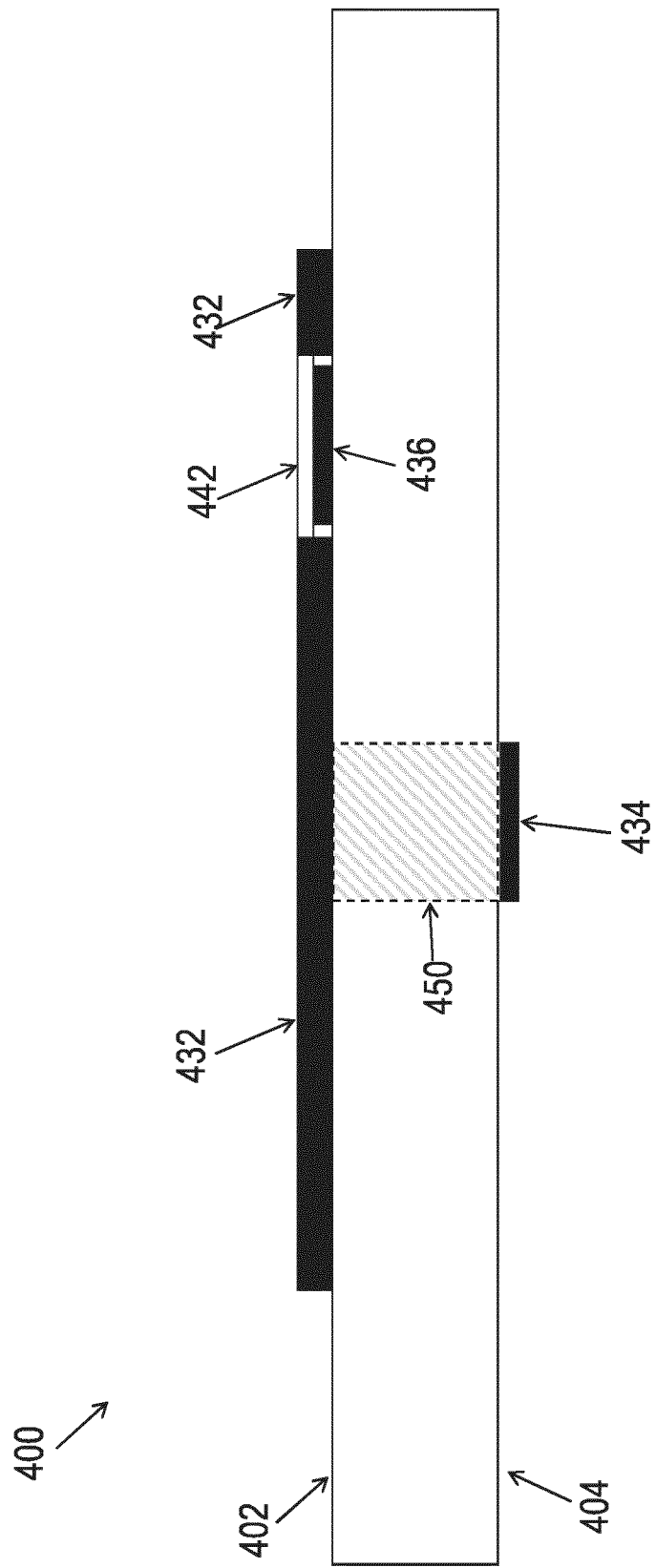

In some cases, track 436 can be positioned on the first side 402 of the substrate 404. As illustrated in FIGS. 14A and 14C, a mask region or mask 442 made of electrically isolating or nonconductive material can be positioned on the substrate 400. The mask 442 can prevent formation of an electrical connection between the tracks 432 and 436. Mask can be positioned in a region where two or more tracks positioned on the same side of the substrate 400 intersect or crossover, but should not be electrically connected. Mask can be positioned between the tracks. Mask can have an area larger than the area of the intersection of the tracks. Mask can be made of nonconductive paint or another nonconductive material.

Additionally or alternatively, to increase the area in which tracks can be routed on the substrate 400 and the area for positioning one or more electronic components, tracks can be routed along the y-axis (such as, left/right or horizontally) on the same size of the substrate (which can be referred to as a first layer) and along the x-axis (or up/down or vertically) on the same side of the substrate (which can be referred to as a second layer). This way, four layer can be formed on the substrate. For example, track 432 is illustrated as being routed along the y-axis (or being positioned in the first layer), and track 436 is illustrated as being routed along the x-axis (or being positioned in the second layer). As described herein, tracks in different layers on the same side of the substrate can be separated by a mask. For example, a mask can be positioned where tracks from first and second layers crossover (unless it is desired for the tracks to be electrically connected). With reference to FIG. 14A, the mask 442 can be positioned between the tracks 432 and 436.

Although track 432 is shown as running in the direction along the y-axis, track 432 can run in a direction along the x-axis. Although tracks 434 and 436 are shown as running in a direction along the x-axis, tracks 434 and 436 can run in a direction along the y-axis.

In some cases, multiple substrates can be stacked. For example, if two substrates are stacked, this can result in formation of four layers (each substrate having top and bottom layer), eight layers (each substrate having top, bottom, first, and second layer), or the like.

Other Variations

Although some of the disclosed embodiments illustrate arrangement of electronic components, such as sensors, in or on a wound dressing, disclosed component arrangements are not so limited. In some implementations, the components can be arranged on another dressing, structure, or substrate or could be provided separately for being positioned over any wound, as broadly defined herein. Component arrangements can be used for one or more of preventing or treating a wound. In addition, embodiments disclosed herein are broadly applicable to any substrate that supports one or more electronic components or connections, whether or not such substrate will be used for monitoring or treating a wound.

Any of the embodiments disclosed herein can be used with any of the embodiments described in International Patent Publication No. WO2017/195038, titled "SENSOR ENABLED WOUND MONITORING AND THERAPY APPARATUS," International Patent Publication No. WO2018/189265, titled "COMPONENT STRESS RELIEF FOR SENSOR ENABLED NEGATIVE PRESSURE WOUND THERAPY DRESSINGS," International Patent Application No. PCT/EP2018/069883, titled "BIOCOMPATIBLE ENCAPSULATION AND COMPONENT STRESS RELIEF FOR SENSOR ENABLED NEGATIVE PRESSURE WOUND THERAPY DRESSINGS," and International Patent Application No. PCT/EP2020/052111, titled "SENSOR INTEGRATED DRESSINGS AND SYSTEMS," each of which is incorporated by reference in its entirety.

In some embodiments, one or more electronic components can be positioned on the side of a substrate the side that faces the wound. Systems and methods described herein are equally applicable to such arrangements of components. Any wound dressing embodiment described herein can include features of any of the other described wound dressing embodiments. Similarly, any controller described herein can include features of any of the other described wound dressing embodiments. Further, any device, component, or module described in a certain embodiment can include features of any of the other described embodiments of the device, component, or module.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A method of manufacturing a wound dressing, the method comprising:

perforating a substantially flexible substrate to form a plurality of openings configured to allow fluid to pass through the substantially flexible substrate, the plurality of openings constraining widths of a plurality of regions located between adjacent rows or columns of openings;

positioning in a first region of the plurality of regions of the substantially flexible substrate a first conductive track configured to be connected to a first sensor, the first conductive track having a first minimum width selected to maintain integrity of a first digital electrical signal conducted by the first conductive track, the first minimum width being constrained by a width of the first region;

positioning in a second region of the plurality of regions of the substantially flexible substrate a second conductive track configured to be connected to a second sensor, the second conductive track having a second minimum width selected to maintain integrity of a second digital electrical signal conducted by the second conductive track, the second minimum width being constrained by a width of the second region;

selecting a third minimum width of a third conductive track to be larger than the first minimum width of the first conductive track and the second minimum width of the second conductive track; and positioning in a third region of the plurality of regions of the substantially flexible substrate the third conductive track configured to be connected to a tissue impedance sensor, the third conductive track having the third minimum width selected to maintain integrity of a third analog electrical signal conducted by the third conductive track, the third minimum width being constrained by a width of the third region, wherein at least one of the first conductive track, second conductive track, or third conductive track is formed from a conductive material selected based on a respective minimum width of the track and a respective minimum width of the region.

2. The method of claim 1, wherein perforating the substantially flexible substrate to form the plurality of openings comprises not perforating the first, second, and third regions of the substantially flexible substrate.

3. The method of claim 1, wherein positioning at least one of the first, second, or third conductive tracks comprises printing the at least one of the first, second, or third conductive tracks using a conductive ink.

4. The method of claim 3, wherein the conductive ink comprises silver ink.

5. The method of claim 1, further comprising positioning in a fourth region of the plurality of regions of the substantially flexible substrate a fourth track configured to provide power to at least one of the first, second, or tissue impedance sensors, the fourth track having a fourth minimum width, the fourth minimum width being constrained by a width of the fourth region.

6. The method of claim 1, wherein the first, second, and third conductive tracks and the first, second, and tissue impedance sensors are positioned at least a minimum distance away from the plurality of openings.

7. The method of claim 1, wherein at least two of the first, second, or third minimum widths are different from one another.

8. The method of claim 1, wherein the first sensor comprises a temperature sensor, and the second sensor comprises a light sensor, and wherein the first and second minimum widths comprise 0.3 mm and the third minimum width comprises 0.5 mm.

9. A wound dressing manufactured using the method of claim 1.

10. The method of claim 1, further comprising:
selecting a first conductive material for forming the first conductive track based on the first minimum width and the width of the first region and forming the first conductive track using the first conductive material; and
selecting a second conductive material for forming the second conductive track based on the second minimum width and the width of the second region and forming the second conductive track using the second conductive material, the second conductive material being different from the first conductive material.

11. The method of claim 10, wherein impedance of the first conductive material is different than impedance of the second conductive material.

12. The method of claim 10, wherein the first conductive material comprises a first conductive ink and the second conductive material comprises a second conductive ink of a different impedance than the first conductive ink.

13. The method of claim 10, further comprising selecting a third conductive material for forming the third conductive track based on the third minimum width and the width of the third region and forming the third conductive track using the third conductive material, the third conductive material being different from the first and second conductive materials.

14. The method of claim 13, wherein impedance of the third conductive material is different than impedance of the first and second conductive materials.

15. A method of manufacturing a wound dressing, the method comprising:
positioning on a side of a substantially flexible substrate a plurality of first conductive tracks oriented in a horizontal direction and configured to transmit electrical signals;
positioning on the side of the substantially flexible substrate a plurality of second conductive tracks oriented in a vertical direction and configured to transmit electrical signals, at least a portion of a second conductive track of the plurality of second conductive tracks crossing over at least a portion of a first conductive track of the plurality of first conductive tracks; and
positioning a nonconductive mask between the at least the portion of the first conductive track of the plurality of first conductive tracks and the at least the portion of the second conductive track of the plurality of second conductive tracks to electrically isolate the first conductive track from the second conductive track.

16. The method of claim 15, further comprising perforating the substantially flexible substrate to form at least one opening in a portion of the substantially flexible substrate separating the first conductive track from the second conductive track.

17. The method of claim 15, wherein positioning the plurality of first conductive tracks comprises printing the plurality of first conductive tracks using a conductive ink, and wherein positioning the plurality of second conductive tracks comprises printing the plurality of second conductive tracks using the conductive ink.

18. The method of claim 17, wherein the conductive ink comprises silver ink.

19. A wound dressing manufactured using the method of claim 15.

20. The method of claim 15, further comprising forming a connection between a third conductive track of the plurality of first conductive tracks and a fourth conductive track of the plurality of second conductive tracks, the connection having a circular shape with a radius that is at least half of a largest width of the third and fourth conductive tracks.

* * * * *